United States Patent [19]
Barrach et al.

[11] Patent Number: 5,541,295
[45] Date of Patent: Jul. 30, 1996

[54] DETECTION OF TYPE II COLLAGEN AND ITS PEPTIDES

[75] Inventors: Hans-Jurgen Barrach, Greenville; Clinton O. Chichester, Wakefield, both of R.I.

[73] Assignees: The Board of Governors For Higher Education State of Rhode Island and Providence Plantations; Rhode Island Hospital, both of Providence, R.I.

[21] Appl. No.: 17,518

[22] Filed: Feb. 12, 1993

[51] Int. Cl.$^6$ ................................................ C07K 16/18
[52] U.S. Cl. ......................... 530/388.1; 530/391.1; 530/391.3; 435/7.93; 435/7.94; 435/70.21; 435/240.27; 435/961; 436/531; 436/548
[58] Field of Search .................... 435/7.92, 7.93, 435/7.94, 70.21, 240.27, 961, 975; 436/518, 531, 536, 548, 808, 811; 530/388.1, 391.1, 391.3

[56] References Cited

U.S. PATENT DOCUMENTS

| | | | |
|---|---|---|---|
| 4,312,853 | 1/1982 | Timpl | 424/540 |
| 4,340,581 | 7/1982 | Timpl | 424/1.57 |
| 4,504,587 | 3/1985 | Timpl et al. | 436/538 |
| 4,565,789 | 1/1986 | Liotta et al. | 436/504 |
| 4,628,027 | 12/1986 | Gay | 435/7.23 |

FOREIGN PATENT DOCUMENTS 8904491   5/1989   WIPO.

OTHER PUBLICATIONS

Holmdahl et al., "Origin of the Autoreactive Anti–Type II Collagen Response I. Frequency of Specific and Multispecific B Cells in Primed Murine Lymp Nodes", *Immunology*, vol. 61, pp. 569–374, (1987).

TIMPL "Immunology of the Collagens", in *Extracellular Matrix Biochemistry*, K. Piez and A. H. Reddi, eds., Elsevier/North Holland Publishers, Amsterdam, (1984), pp. 159–190.

Hollister et al., "Production and Chracterization of Hybridoma Antibody to Native Human Tpe II Collagen", Collagen and Related Research, vol. 2, 1982, pp. 197–210.

Linsemayer, et al. "Monoclonal Antibodies to Connective Tissue Macromolecules: Type II Collagen", Biochemical and Biophysical Research Communication, vol. 92, No. 2, 1980, pp. 440–446.

Terato, et al. "Physicochemical and Immunological Studies on the Renatured β 1(II) Chains and Isolated Cyanogen Bromide Peptides of Type II Collagen", Collagen and Related Research, vol. 5, 1985, pp. 469–480.

Bellon, G., *Analytical Biochemistry* 150:188 (1985).
Black, D., et al, *Analytical Biochem.*, 169:197 (1988).
Chichester, C. et al, *J. of Immun. Methods*, 140:259 (1991).
Dodge, G. R., et al., *J. Clin. Invest.*, 83:647 (1989).
Dusemund, B., et al., *J. of Immun. Methods*, 50:255 (1982).
Hanson, D. A., et al, *Journal of Bone and Mineral Research* 7:1251 (1992).
Kittelberg–Ewer, R. et al, *Immunological Investigations*, 17(1):49 (1988).
Miller, E. J., *Biochemistry*, 10:3030 (1971).
Moreland, L. W., et al., *Arthritis and Rheumatism*, 32:1458 (1989).
Posner, M. R., et al., *Hybridoma*, 8:187 (1989).
Robins, S. P., *Biochem. J.*, 207:617 (1982).
Robins, S. P., et al., *Annals of the Rheumatic Diseases*, 45:969 (1986).
Srinvas, G. R., et al., *Journal of Immunological Methods*, 159:53 (1993).
Wu, J. J., et al., *Biochemistry*, 23:1850 (1984).

*Primary Examiner*—Lila Feisee
*Assistant Examiner*—Susan C. Wolski
*Attorney, Agent, or Firm*—Fish & Richardson

[57] ABSTRACT

The invention discloses monoclonal antibodies which bind specifically to Type II collagen, but not to its peptides, or vice versa. Also disclosed are the methods of preparing hybridomas for production of these antibodies; the assays which utilize these antibodies to detect or quantify Type II collagen and/or its peptides in a solution (e.g., body fluid, culture medium, and tissue extract); and assay kits containing these antibodies.

3 Claims, 20 Drawing Sheets

DETECTION OF TYPE II COLLAGEN AND ITS PEPTIDES

FIELD OF THE INVENTION

The present invention relates to antibodies to cartilage collagen in native, denatured or peptide form and the preparation and use of such antibodies.

BACKGROUND OF THE INVENTION

The use of monoclonal antibodies against connective tissue proteins to establish the collagen profile of histological, cytological and biological fluid samples is an advantageous approach to disease diagnosis and therapy monitoring. Because of the high specificity and sensitivity of monoclonal antibodies, early detection of certain collagen-related pathological conditions is possible as is early assessment of the efficacy of certain therapeutic programs.

The fusion of mouse myeloma cells to spleen cells from immunized mice by Köhler and Milstein in 1975 [Nature 256:495 (1975)] demonstrated for the first time that it was possible to obtain continuous cell lines making homogeneous (so-called "monoclonal") antibodies. Since this nominal work, much effort has been directed toward the production of various hybrid cell lines (also called "hybridomas") and to the use of the antibodies made by these hybridomas for various scientific investigations. While the general technique for the preparation of hybridomas and monoclonal antibodies is well known, there are many difficulties met and variations required for each specific case. There is no assurance, prior to attempting to prepare a given hybridoma, that the desired hybridoma will be obtained, that it will produce antibody if obtained, or that the antibody so produced will have the desired specificity. In fact polyreactive monoclonal antibodies are a major obstacle in the generation of specific monoclonal antibodies to collagen Type II. Chichester et al. J. Immunol. Methods 140:259 (1991).

Immunoassays utilizing polyclonal antibodies have been previously described for the measurement of collagen types I, II and III [Henrotin et al. J. Immunoassay 11(4):555 (1990); Gosslau et al. J. Immunol. Methods 29:71 (1979); Rennard et al., Anal. Biochem. 104:205 (1980); and Bellon, Anal. Biochem. 150:188 (1985)], and propeptides of collagen types I and III [Parfitt et al. J. Bone Mineral Res., 2:427 (1987); and Petersen et al. Arth. Rheum. 29:592 (1986)]. Potential disadvantages in employing polyclonal antibodies for developing immunoassays are their heterogeneous composition and variation in the consistency of sera from animal to animal.

Monoclonal antibodies are ideal for employment in quantitative assays because they are epitope defined and can detect minor structural differences between individual types of collagen. However, the testing for monospecificity of monoclonal antibodies needs to be extensive. Once characterized, monoclonal antibodies can be produced with uniform consistency in large quantities for use in immunoassays and do not require serial affinity chromatography purification.

Chondrocyte cultures are routinely employed for the screening of antiarthritic agents. In primary chondrocyte culture systems, collagen other than Type II can be present in relatively high levels. Chondrocytes in culture tend to change phenotype over time switching from Type II collagen to Types I and III producing cells. In primary chondrocyte cultures, fibroblast contamination is also a common occurrence. Fibroblasts produce collagen Types I, III, IV, V and VI which can interfere with the measurement of Type II collagen. Thus, a sensitive method is required to detect different types of collagen (or degradative peptides thereof) in chondrocyte cultures.

The identification and quantitation of collagen Type II derived peptides in serum, lavage fluids of joints, or synovial fluids of animal models with experimental arthritis or humans with arthritis will provide new and important information on pathogenesis of the disease (e.g., which enzymes are involved in the degradation process), and on the severity of the degradation of cartilage at that time point. The collagen peptide concentration in serum will provide information on the effectiveness of drug treatment on cartilage collagen breakdown and collagen peptide release into body fluids. The ease of taking blood samples from patients or experimental animals will allow a close monitoring of the cartilage destruction.

SUMMARY OF THE INVENTION

An aspect of the present invention relates to immunoassay methods for detecting Type II collagen or its peptides.

One of such methods can be used to detect Type II collagen in a tissue sample. The method includes the steps of degrading the Type II collagen into Type II collagen peptides either by chemical degradation such as cyanogen bromide (CNBr) digestion or by use of a protease under proper conditions; contacting the Type II collagen peptides with a monoclonal antibody which is capable of binding to one of the Type II collagen peptides but not to Type II collagen to form an antibody-peptide complex; and detecting the Type II collagen based on the formation of the antibody-peptide complex.

Another method of this invention can be used to detect Type II collagen peptides in a solution such as biological fluid, e.g., serum, synovial fluid, lavage fluid or medium in a chondrocyte culture or an organ culture. Organ cultures which are known to contain Type II collagen peptides include those of articular cartilage, bovine nasal cartilage and growth plate. The method includes the following steps: separating the Type II collagen peptides from other components, if necessary; contacting the Type II collagen peptides with a monoclonal antibody which is capable of binding to one of the Type II collagen peptides but not to Type II collagen to form an antibody-peptide complex; and detecting the Type II collagen peptides based on the formation of the antibody-peptide complex.

A further method of this invention can be used to detect Type II collagen in a sample and includes the steps of contacting the solution with a monoclonal antibody which is capable of binding to Type II collagen but not to Type II collagen peptides to form an antibody-Type II collagen complex; and detecting the Type II collagen based on the formation of the antibody-Type II collagen complex.

Note that the term "detecting" herein refers to either identification or quantitation of Type II collagen or its peptides. When a monoclonal antibody has association constant (Ka) of at least $10^7$ liters/moles or preferably, 10 liters/moles, for an antigen (e.g., native collagen or collagen peptides), it is said to be capable of binding to that antigen. On the other hand, when a monoclonal antibody has a Ka value of at least most $10^2$ liters/moles or lower for an antigen, it is said to be not capable of binding to that antigen.

In the detecting step of each of the above-described methods, the Type II collagen or its peptides are detected by binding a detectable second antibody to the antibody-peptide complex. Examples of such a detectable second antibody include enzyme-linked antibody, radioactively labeled antibody, and fluorescently labeled antibody. The enzyme and the radioactive or fluorescent label can be attached to the second antibody either directly or indirectly (e.g., avidin biotin or strepavidin biotin detection system). Also, in the contacting step both the antigen and the monoclonal antibody can be in a solution. If desired, that solution can subsequently be transferred to a support coated with the same antigen as in the inhibition enzyme-linked immunosorbent assay ("ELISA"). Alternatively, one of the monoclonal antibody or the antigen is immobilized onto a support. When an antigen is to be immobilized, it is preferred that before immobilization, the antigen (i.e., Type II collagen or its peptides) is partially purified (e.g., by acid precipitation, electrophoresis or affinity beads). The term "support" in this disclosure refers to materials capable of binding proteins, e.g., nitrocellulose membrane, polyvinylidene difluoride membrane, or a container such as a microtiter plate.

Another feature of this invention relates to kits which can be used to conveniently carry out the above-described methods.

For example, a kit for detecting Type II collagen peptides may include (1) a first monoclonal antibody capable of binding to a Type II collagen peptide, but not to Type II collagen or a support coated with the first antibody; and (2) a second monoclonal antibody conjugated to a signal-producing label, the second monoclonal antibody being capable of binding to the same Type II peptide, but to a site different from (i.e., spaced from) that to which the first monoclonal antibody binds. Preferably, the second monoclonal antibody is capable of binding to the pyridinium ring of Type II collagen (e.g., its epitope includes the ring and amino acid residues attached thereto). Such a monoclonal antibody can be prepared by methods well known in the art. See Hanson, D. A. J. Bone and Mineral Res. 1251 (19, hereby incorporated by reference. Also, see Black D. et al. 169:197 (1988) and Robins S. P. Biochem. J. 207:617 (1982), both of which are also incorpoated by reference. This kit is most suitable for carrying out a two-antibody sandwich immunoassay, e.g., two-antibody sandwich ELISA.

Another kit of this invention, which can also be used to detect Type II collagen peptides, includes: (1) a first monoclonal antibody capable of binding to a Type II collagen peptide, but not to Type II collagen or a support coated with the first antibody or a support coated with the first antibody; and (2) a second monoclonal antibody conjugated to a signal-producing label, the second antibody being capable of binding to the first monoclonal antibody.

The two kits described above are to be used for detecting Type II collagen peptides. For detecting Type II collagen, it is preferred to have a kit which includes (1) a first monoclonal antibody capable of binding to Type II collagen, but not capable of binding to Type II collagen peptides or a support coated with the first antibody; and (2) a second monoclonal antibody conjugated to a signal-producing label, the second antibody being capable of binding to the first monoclonal antibody.

In each of the above-described assay kits, the signal-producing label linked to the second antibody can be an enzyme (e.g., horseradish peroxidase or alkaline phosphatase). Preferably, both enzyme and its substrate are provided in the kit. If desired, an uncoated support can also be included in the kit onto which the Type II collagen or its peptides to be detected can be immobilized by the user.

Also within this invention is a monoclonal antibody which is capable of binding to a Type II collagen peptide (e.g., generated by CNBr digestion), but not capable of binding to Type II collagen; or an Fab, F(ab')$_2$ or Fv fragment of such a monoclonal antibody. The binding site of this monoclonal antibody may be within one of the following two sequences: Gly-Phe-Gln-Gly-Leu-Xaa-Gly-Xaa-Xaa-Gly-Xaa-Xaa-Gly SEQ. ID NO:1 and Gly-Leu-Gln-Gly-Leu-Xaa-Gly-Xaa-Xaa-Gly-Xaa-Ser-Gly SEQ. ID No:2, wherein Xaa is Pro or hydroxyproline ("Hyp").

Furthermore, also included in the present invention is a monoclonal antibody which is capable of binding to Type II collagen, but not capable of binding to Type II collagen peptides; or an Fab, F(ab')$_2$ or Fv fragment of such a monoclonal antibody.

Both of these monoclonal antibodies preferably are produced by murine hybridoma cell lines and can be of any Ig class, e.g., IgG.

A method for generating hybrid cells for production of a monoclonal antibody which is capable of binding to a Type II collagen peptide, but not capable of binding to Type II collagen includes the following steps: (a) immunizing an animal with Type II collagen peptides (conjugated to a carrier such as protein as immunogen, if necessary) or denatured Type II collagen; (b) harvesting an antibody-producing organ from the immunized animal; (c) preparing a cellular homogenate from the organ; (d) fusing the cellular homogenate with cultured cancer cells; and (e) selecting hybrid cells which produce monoclonal antibody specific for at least one of the Type II collagen peptides or the denatured collagen, but not for native Type II collagen. Preferably, in the immunizing step the animal is immunized with a substantially purified CB9,7 (see discussion below) or with a substantially purified peptide containing a sequence selected from the group consisting of Gly-Phe-Gln-Gly-Leu-Xaa-Gly-Xaa-Xaa-Gly-Xaa-Xaa-Gly SEQ. ID NO:1 and Gly-Leu-Gln-Gly-Leu-Xaa-Gly-Xaa-Xaa-Gly-Xaa-Ser-Gly, SEQ ID NO:2 wherein Xaa is Pro or Hyp. Denatured Type II collagen can be obtained by heating at 60° C. for one hour to disrupt the secondary structure of the native collagen. Note that unless specified, the term "Type II collagen" refers to its native form.

A similar method can be used for generating hybrid cells for production of a monoclonal antibody which is capable of binding to Type II collagen, but not capable of binding to Type II collagen peptides, except that an animal is immunized with Type II collagen and that the selecting criteria are different.

Other features and advantages of the present invention will be apparent from the following drawings and description of the preferred embodiments, and also from the appending claims.

BRIEF DESCRIPTION OF THE DRAWING

The drawings are first described.

DESCRIPTION OF THE PREFERRED EMBODIMENTS

Figure 1A:
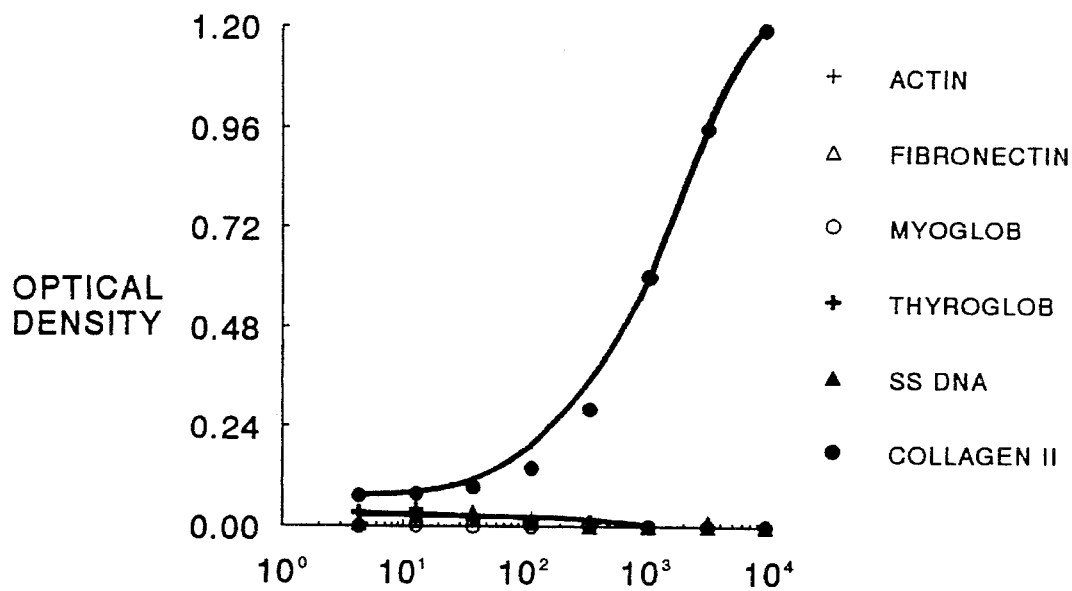
FIG. 1 is a set of graphs showing specificity of the monoclonal antibodies C4F6 and E1E5.
Figure 1B:
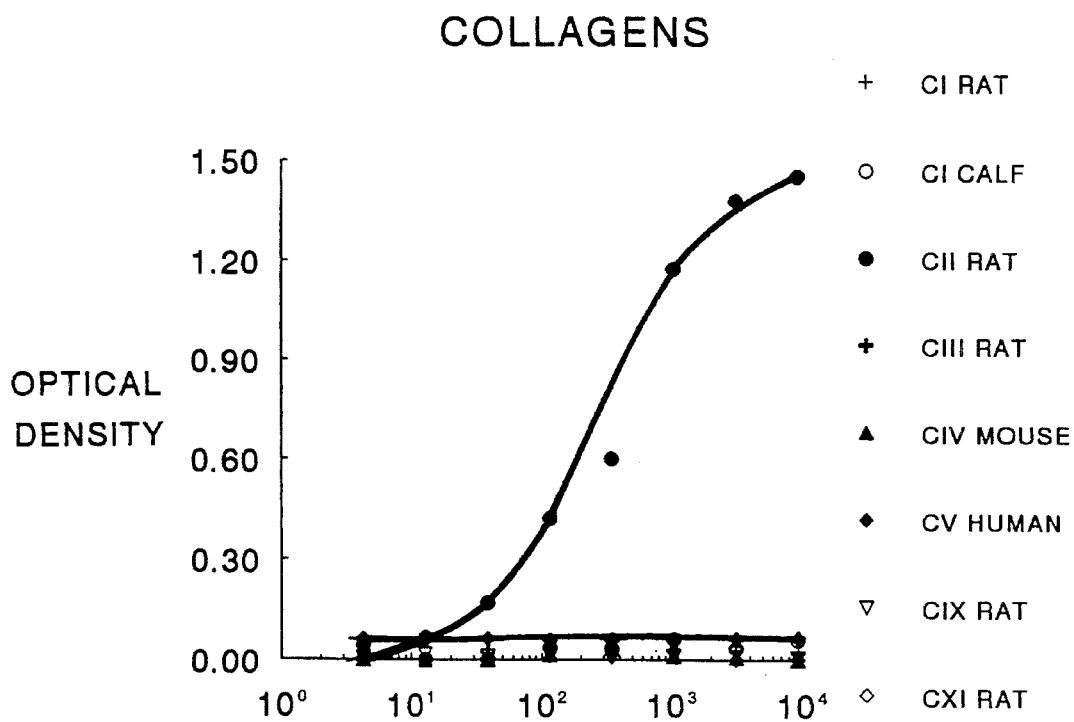
Figure 1C:
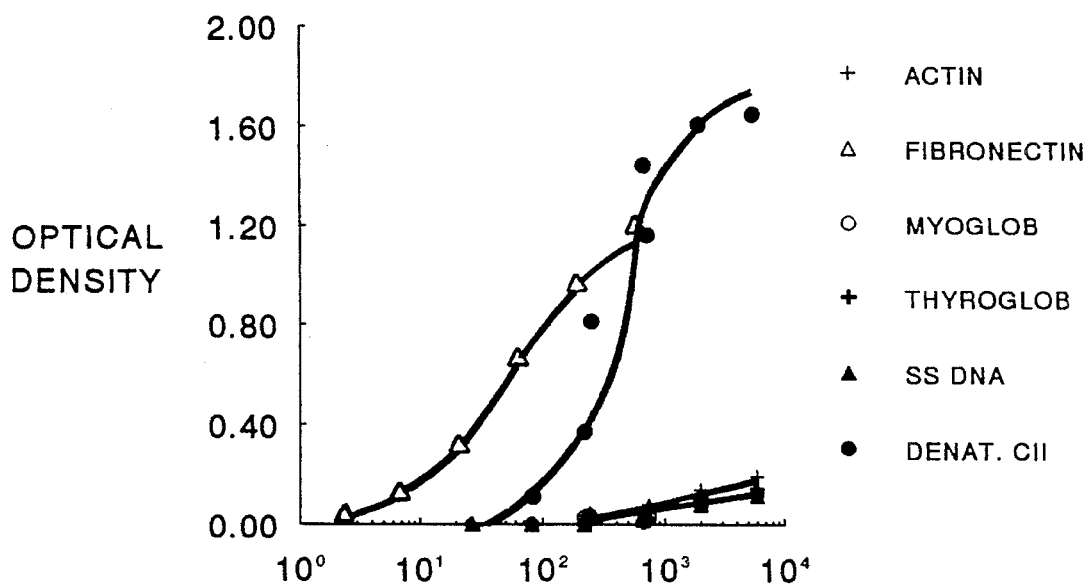
Figure 1D:
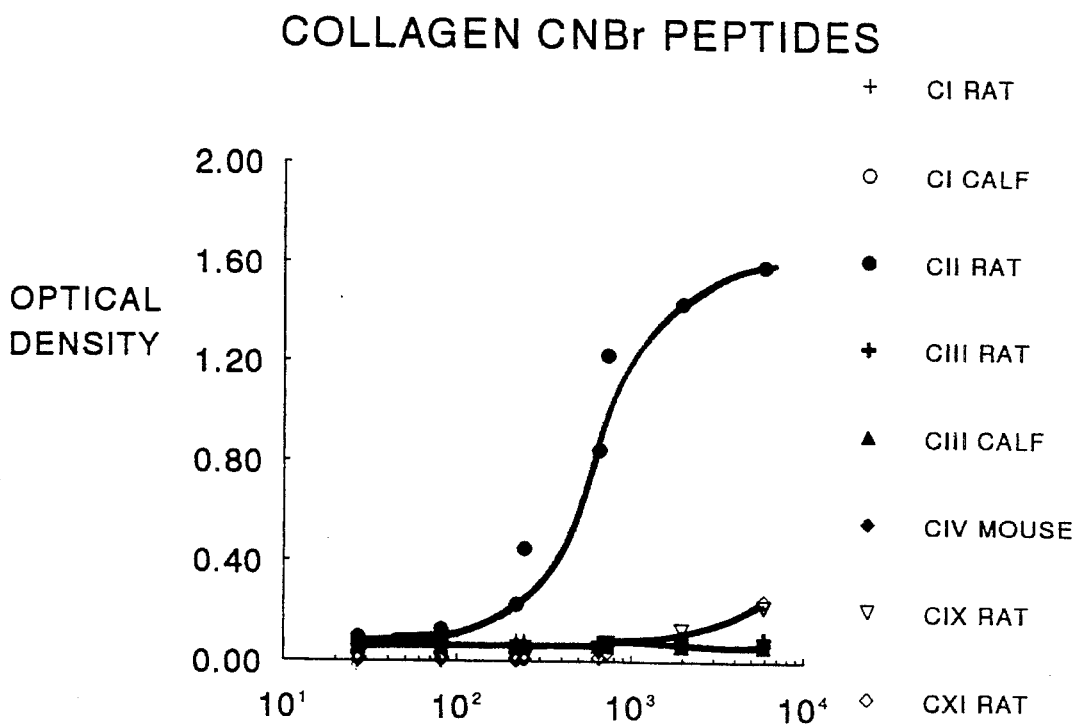

The invention embodies monoclonal antibodies which bind specifically to Type II collagen, but not to its peptides, or vice versa; the methods of preparing hybridomas for production of these antibodies; the assays which utilize these antibodies to detect or quantitate Type II collagen and/or its peptides in a solution (e.g., culture medium, tissue extract and biological fluid); and assay kits containing these antibodies.

Following procedures disclosed below, we were able to generate hybridomas capable of producing monospecific monoclonal antibodies reactive with Type II collagen and Type II collagen peptides, respectively. For example, hybridomas C4F6 and E6E3 bind specifically to Type II collagen, but not to Type II collagen peptides. On the other hand, hybridomas E1E5 and E4A11 bind specifically to Type II collagen peptides, but not to Type II collagen. Antibodies produced by such hybridomas can be employed in the quantitation of Type II collagen and its peptides. Note that the code names C4F6, E6E3, E1E5 and E4A11 are used herein to refer to both the hybridomas and the antibodies produced by them.

The immunoassays described below, which take advantage of the high specificity and affinity of such monoclonal antibodies, can be utilized for the measurement of native Type II collagen and its cyanogen bromide derived peptides and naturally derived peptides in body fluids, chondrocyte cultures in very low concentrations.

Quantitative assays developed with antibodies C4F6 and E6E3 of the invention are well suited for the measurement of Type II collagen synthesis in chondrocyte culture systems. The assays developed with monoclonal antibodies required very little sample volume and quantify low nanogram concentrations of Type II collagen in culture samples without the interference of fetal calf serum which is present in most culture medium. The precision and reproducibility of these assays was determined in culture medium under conditions that were in close approximation to the actual sample composition. The Swarm rat chondrosarcoma offers advantages such as easy propagation and a high yield of chondrocytes. This culture system lends itself to routine screening and can be used to examine the effects of a variety of agents on Type II collagen synthesis.

At concentrations optimal for the quantification of collagen Type II or its peptides, the antibodies C4F6 and E6E3 do not exhibit any reactivity to various minor cartilage collagen nor to collagen I, III and IV and V produced by fibroblasts. These quantitative assays thus can be employed to measure Type II collagen in chondrocyte cultures in the presence of a relative abundance of other collagen types.

Quantitative assays developed with antibodies E1E5 and E4A11 can be utilized, along with CNBr digestion, for the estimation of Type II collagen levels in tissue samples. In cartilage, Type II collagen exists in a highly cross-linked fibrillar form and has poor extractability. CNBr digestion can be employed to solubilize Type II collagen, by cleaving collagen fibrils into small soluble peptides. These peptides can then be quantified by inhibition ELISA or Western blot. Antibodies E1E5 and E4A11 specifically react to Type II collagen peptides present in CNBr digests of rat, bovine, rabbit, and human cartilages. They are identified by Western blot technique as CBe, CB9,7 and cross-link involving CB8 and/or CB9,7 (see discussion below). These antibodies have the potential for application in animal models such as adjuvant induced arthritis in rats or the Hulth model of osteoarthritis in rabbits. These assays can be used for the direct measurement of Type II collagen in cartilage samples with minimal processing. Assays of the invention include sensitive methods involving these antibodies employing CNBr digestion or other articular cartilage samples and subsequent analysis either by sodium dodecylsulfate-polyacrylamide gel electrophoresis ("SDS-PAGE") followed by Western blot, or by dot blot or slot blot assays.

Naturally occurring collagen Type II peptides in biological fluids can be identified and quantified with the antibodies E1E5 and E4A11 with modified standard immunoassays. For example, after elimination of most serum proteins by trichloroacetic acid ("TCA") precipitation and centrifugation, the peptides can be determined by ELISA, Western blot or slot blot assays of the supernatant.

Monoclonal antibody—development and characterization

The hybrid cell lines of the present invention may be produced by various methods generally known to those of ordinary skill in the art. In general, the method involves immunizing suitable mammals (for example, mice) with the antigens of interest, in this case collagen antigens, fusing antibody producing cells isolated from the spleen of the animal with myeloma cells, cloning the resulting hybrid cells and selecting those cells which produce the desired monoclonal antibody which binds the antigen of interest.

Immunizations are usually performed with purified antigens. To increase the antigenicity of collagen, immunizations are performed using the Type II collagen conjugate. Glutaraldehyde may be employed to conjugate Type II collagen to carrier molecules, or Type II collagen can be cross-linked to itself.

The usual mammals used for immunizations are mice, especially CD-1 mice, but other mammals and mouse strains may also be employed. The immunizations are performed in a manner known in the art, such as by administering intraperitoneally, intravenously and/or subcutaneously three to six injections each containing an appropriate amount of purified antigen (i.e., from about 1 mg to about 50 mg) at intervals of about one to six weeks, usually together with an adjuvant that stimulates the production of lymphocytes, e.g., complete or incomplete Freund's adjuvant.

Antibody-producing cells present in the spleen of the immunized animals are taken from the animals two to six days after the last ("booster") immunization and fused with myeloma cells of a suitable cell line. Myeloma cell lines and cell lines derived therefrom are known as suitable fusion partners. The myeloma cell line is generally derived from the same species as the immunized mammal, since intraspecies hybrids are more viable than inter-species hybrids.

Myeloma cells that lack the enzyme hypoxanthine-guaninephosphoribosyl transferase (HGPRT) or the enzyme thymidine kinase (TK) and which do not survive in a selective culture medium containing hypoxanthine, aminopterin and thymidine (HAT medium), can be employed. Myeloma cells and cell lines prepared therefrom that do not survive in HAT medium and do not secrete any immunoglobulins or parts thereof, for example, cell lines X63-Ag8.653 and SP2/0-Ag14, can also be used. Various fusion-promoters, for example, Sendai virus or other paramyxoviruses, optionally in UV-inactivated form, calcium ions, surface-active lipids, such as isolecithin, or polyethylene glycol ("PEG") may also be employed. Myeloma cells are usually fused with a three-to twenty-fold excess of spleen cells from immunized animals in a solution containing from about 30 to 50% PEG having a molecular weight of about 1000 to 4000. Exposure to PEG for about 2 to 3 minutes appears to be optimal to prevent toxicity to the cells; temperatures of about 37° C., are recommended. After fusion the cells are partitioned out and cultured in selective HAT medium.

Suitable culture media for the growth of the hybrid cells are the customary standard culture media, for example, RPMI Medium or medium containing 20% fetal calf serum which is supplemented with antibodies. At the beginning of cell growth, so-called feeder cells (e.g., normal mouse peritoneal exudate cells, spleen cells, bone marrow macrophages or the like) can be added. At regular intervals, the culture media may be supplemented by selective HAT medium to prevent hybrid cells from being overgrown by ordinary myeloma cells.

The cell culture supernatants of the hybrid cells surviving HAT selection are examined for the presence of the desired monoclonal antibodies. Advantageously, the cell supernatants are tested in an immunoassay, for example, enzyme immunoassay, that demonstrates the binding of monoclonal antibodies to the antigen of interest.

Those hybridomas which produce antibodies having the desired specificity as well as other desirable characteristics can then be maintained as viable cultures and/or frozen for storage.

Large quantities of the desired monoclonal antibodies can also be obtained by multiplying the hybridoma cells in vivo. For this purpose, antibody producing hybridomas are inoculated intraperitoneally into syngenic mammals, and after 1 to 3 weeks, the antibodies are isolated from ascites fluid of those mammals. For example, hybrid cells originating from CD-1 mice can be injected intraperitoneally into CD-1 mice that have previously been pretreated intraperitoneally with a hydrocarbon such as 2,6,10,14-tetramethylpentadecane (pristane) to prevent fluid drainage from the intraperitoneal cavity, and after 8 to 10 days, ascites fluid is taken from these animals.

The monoclonal antibodies produced in vitro or in vivo may be purified using various methods, for example, affinity chromatography, gel filtration chromatography, ion-exchange chromatography or DEAE-cellulose chromatography. Optionally, selected proteins in the culture supernatants or ascites fluid, including the desired monoclonal antibodies, may be precipitated using specific concentrations of ammonium sulphate or the like before being subjected to chromatography.

The present invention encompasses all monoclonal antibodies exhibiting the characteristics of monoclonal antibodies described herein. In other words, antibodies having the patterns of reactivity illustrated herein are within the scope of the invention regardless of the immune globulin class or subclass to which they belong. For example, a monoclonal antibody exhibiting the characteristic described herein may be of class $IgG_1$, $IgG_2a$, $IgG_2b$, $IgG_3$, or of classes IgM, IgA, or of other known Ig classes. Furthermore, while a hybrid cell line generated from a known mouse myeloma and spleen cells from a known species of immunized mouse cannot be further identified except by reference to the antibody produced by that specific hybrid cell line, all hybrid cell lines producing antibodies having the reactivity characteristics described above are within the present invention.

EXAMPLE 1

Purification of Type II collagen and preparation of CNBr peptides

Type II collagen was prepared from the Swarm rat chondrosarcoma (Smith et al. Arch. Biochem. Biophys. 166:181 (1975). Briefly, after extracting the tumor in guanidine. HCl, pepsinization in 0.5 M acetic acid was carried out at 4° C. for 24 hours. After centrifugation, the supernatant was neutralized with NaOH, and the collagen precipitated from the supernatant with 4.5 M NaCl. The precipitate was then dissolved in 0.5 M acetic acid, dialyzed into neutral buffer. The Type II collagen was further purified by successive salt precipitations at neutral pH [Trelstad et al., Anal. Biochem. 71:114 (1976), freed from proteoglycans by DEAE-cellulose chromatography (Miller, E. J. Biochem. 10 (Suppl.) 1652 (1971)], precipitated by dialyzing against 20 mM $Na_2HPO_4$, dissolved in 0.5 M acetic acid and finally precipitated with 5% NaCl. The precipitate was dialyzed against 0.15 M acetic acid and lyophilized. The Type II collagen preparation showed no impurities upon analysis by 6% SDS-PAGE. Denatured Type II collagen was prepared by heating for 1 hour at 60° C. CNBr peptides were prepared according to the method of Kittelberger (Kittelberger et al. Prep. Biochem. 16:81 (1988) from purified Type II or other collagen.

Immunization and hybridoma screening procedure

Mice CD-1 (Charles River) were used for immunization. The mice were cared for in accordance with institutional guidelines. Type II collagen, purified from rat chondrosarcoma, was cross-linked to itself or hemocyanin using glutaraldehyde and the conjugates were dissolved in 0.1M acetic acid at 1 mg/ml concentration. Each collagen conjugate was mixed with equal volume of complete Freunds adjuvant for immunization. CD-1 mice between 6 and 8 weeks of age were injected subcutaneously with 50 mg of Type II collagen in complete Freunds adjuvant at two different sites. This was followed by four booster injections administered in incomplete adjuvant at three week intervals. Mice with high antibody titer to Type II collagen were given a final booster injection via a foot pad injection. Hong et al, J. Immunol. Methods, 120:151 (1989); Holmdahl et al., J. Immunol. Methods 83:379 (1985). A single injection of Type II collagen prepared in complete Freunds adjuvant was administered into each of the hind foot pads. After 9–11 days, the popliteal lymph nodes were isolated and used for fusions.

Cultures were grown in RPMI medium supplemented with glutamine, gentamycin and 20% calf serum (Hyclone Laboratories). Fusions were performed by mixing lymph node cells with myeloma cells (X63-653-AgS) in a ratio of 2:1 in 50% w/v PEG. The cells were suspended in HAT media (hypoxanthine, aminopterin and thymidine) and distributed (100 ml/well) to 96 well microtiter plates. The plates were incubated at 37° C., 5% $CO_2$. After one week the media were changed to media containing hypoxanthine and thymidine. After approximately two weeks the cultures were screened by ELISA for the presence of Type II collagen reactive antibodies. Hybridoma cultures producing Type II collagen reactive antibodies were tested for reactivity to thyroglobulin to exclude cell lines producing polyreactive antibodies. Hybridomas from wells that tested positive for reactivity to Type II collagen and negative for thyroglobulin were cloned at least three times to ensure monoclonality. The specificity of these monoclonal antibodies was then tested on microtiter plates coated with different collagen and non-collagenous antigens.

ELISA for the detection of Type II collagen antibodies

Hybridoma supernatants containing Type II collagen antibodies were incubated for 1 hour at room temperature in wells of microtiter plates (Corning, 25801) previously coated with either native or denatured Type II collagen (100 μl/well at 10 ∞g/ml in 0.1M sodium carbonate, pH 9.6 overnight at 4° C.). After washing the microtiter plates with PBS (phosphate buffered saline)-0.05% Tween pH 7.6, the bound antibodies were detected by adding goat anti-mouse IgG conjugated to horseradish peroxidase (Zymed) and incubated for 1 hour at room temperature. The peroxidase activity retained in each well was measured colorimetrically using tetramethylbenzidine (TMB) as substrate (Bos et al. J. Immunoassay 2:187 (1981).

Antibody purification and isotype determination

Monoclonal antibodies were purified from the culture supernatants by affinity chromatography on Type II collagen-Sepharose or Protein A-Sepharose columns. The isotypes of the antibodies were analyzed by the Ouchterlony immunodiffusion technique, using specific goat anti-mouse IgM and anti IgG isotype antibodies. Protein concentrations of the purified antibody preparations were determined using the bicinchoninic acid method (Smith, Anal. Biochem. 150:76 (1985).

Specificity testing

Four monoclonal antibodies that were monospecific to Type II collagen or its CNBr peptides were chosen for assay development and identified as C4F6, E1E5, E6E3 and E4A11.

More specifically, microtiter plates were coated with the appropriate antigen by overnight incubation at 4° C. in a volume of 100 μl of a 10 μg/ml solution dissolved in 0.1M sodium carbonate buffer pH 9.6. Coating concentrations were 10 mg/ml for most antigens except for collagen (2 ∞g/ml) or denatured or cyanogen bromide peptides (0.5 μg/ml). The purified monoclonal antibodies were then tested for reactivity on these plates using an ELISA. The plates were washed with PBS-0.05% Tween pH 7.6 and various dilutions of mouse monoclonal antibody in PBS-0.05% Tween pH 7.6 were incubated for 1 hour at room temperature. The bound immunoglobulins were detected by incubating with goat anti-mouse IgG horseradish peroxidase conjugate for one hour at room temperature. The plates were further washed with PBS-0.05% Tween buffer and the optical density was measured colorimetrically upon incubation with buffered substrate.

FIG. 1 shows the reactivity of the monoclonal antibodies, C4F6 and E1E5, to various collagen and non-collagenous antigens was determined by ELISA. FIGS. 1A and 1B show concentration dependent binding of purified monoclonal antibody C4F6 to various antigens coated on the microtiter plates: actin, thyroglobulin, fibronectin, myoglobin, ssDNA and native Type II collagen (FIG. 1A) and rat collagen types I, II, III, IV, IX, XI, mouse collagen type IV, calf collagen type I, and human type V collagen (FIG. 1B). The binding profile of Type II collagen peptide-specific antibody E1E5 are shown in FIGS. 1C and 1D: actin, thyroglobulin, fibronectin, myoglobin, ssDNA, denatured Type II collagen (FIG. 1C) and the CnBr peptides of rat collagen types I, II, III, IV, IX, XI and cyanogen bromide peptides of calf collagen types I and III (FIG. 1D).

Antibodies C4F6 and E6E3 reacted preferentially with Type II collagen in the native configuration while antibodies E1E5 and E4A11 showed specificity to Type II collagen in the denatured form and to CNBr peptides of collagen II (CII). See Table I. Results from cross species reactivity testing indicated that all four monoclonal antibodies displayed good reactivity to Type II collagen or Type II collagen CNBr peptides obtained from rat, rabbit, bovine, chick or human sources. The only exception was that C4F6 did not react with chicken Type II collagen.

TABLE I

Comparison of the Type II Collagen Quantitative
Assays Developed with Specific Monoclonal Antibodies

| Antibody | C4F6 | E6E3 | E1E5 | E4A11 |
|---|---|---|---|---|
| Antibody Isotype | IgG1 | IgG1 | IgG1 | IgG1 |
| Site of Binding | CB11 | CB11 | CB8; 9,7 | CB8; 9,7 |

TABLE I-continued

Comparison of the Type II Collagen Quantitative
Assays Developed with Specific Monoclonal Antibodies

| | | | | |
|---|---|---|---|---|
| Affinity to Type II collagen Kd value@ (moles/liter) | $5.31 \times 10^{-10}$* | $6.16 \times 10^{-10}$* | $4.41 \times 10^{-9\dagger}$ | $2.73 \times 10^{-9\dagger}$ |
| Optimal assay parameters | | | | |
| Antibody concentration | 238.7 ng/ml | 32.9 ng/ml | 9.28 ng/ml | 16.3 ng/ml |
| Antigen coating | 2.0 µg/ml | 2.0 µg/ml | 0.5 µg/ml | 0.5 µg/ml |
| IC-50 values of optimized inhibition ELISAs | | | | |
| Native Type II Collagen | 42 ng/ml | 206 ng/ml | — | — |
| Denatured Type II Collagen | — | — | 400 ng/ml | 500 ng/ml |
| CNBr Peptides of Type II | — | — | 240 ng/ml | 210 ng/ml |

*native Type II collagen
†denatured Type II collagen
determined by western blotting of Type II collagen derived CnBr peptide fragments
@determined according to the method of Friguet et al. (1985)

Inhibition ELISA and determination of IC-50 Values

Monoclonal antibodies diluted in DME with 10% fetal calf serum were mixed with equal but separate volumes of medium containing increasing amounts of native or denatured Type II collagen or Type II collagen CNBr peptides. The samples were preincubated overnight at room temperature. The mixtures were transferred to ELISA plates precoated with the same antigen employed in the overnight preincubation step. After a thirty minute further incubation on the microtiter plates and washing with PBS-0.05% Tween, the monoclonal antibodies which bound to solid phase antigens were measured with ELISA. The IC-50 values were determined by estimating the antigen concentration required to produce a 50% inhibition of the maximal response (Table I).

Epitope determination by Western blot

CNBr peptides of collagen Type II were used to determine the binding site of the antibodies. For CNBr digestion of collagen, see Miller, E. J. Biochem. 10:3030 (1971), hereby incorporated by reference. The CNBr peptides were separated by SDS-PAGE in 16% acrylamide gels (BioRad Mini Gel System) and electro blotted onto nitrocellulose membrane. The membrane was blocked with 5% non-fat milk washed 3 times with PBS-Tween, incubated with the monoclonal antibody in PBS-Tween 1 hour. The membrane was washed three times with PBS-Tween and the bound antibody was detected using goat anti-mouse IgG peroxidase labeled antibody and a mixture of 4-chloro-1-naphthol and 3.3'-diaminobenzidine and $H_2O_2$ as substrates. The binding site results are summarized in Table I. The respective molecular weights of CB11, CB9,7 and CB8 are about 27,000, 11,600 (7,200 and 4,400) and 15,000.

The antibodies C4F6 and E6E3 stained very lightly the band corresponding to CB11 [Miller, E. J. Id. and Morgan, K. Immunology 77:609 (19923, both of which are incorporated by reference in their entirety]. This light staining may reflect that only few epitopes remain after SDS-PAGE and electroblotting. In ELISA these two monoclonal antibodies react only with native (not denatured) collagen Type II.

The monoclonal antibodies E4A11 and E1E5, specific for denatured collagen Type II and its CNBr peptides, stained CB8 very prominently. Less intense staining was found above and below CB8 and in uncleaved collagen bands larger than CB10 (M.W. -32,000). Mature collagen Type II fibrils contain nonreducible cross-links which are stable during cyanogen bromide cleavage. Pyridinoline cross-links, a major intermolecular cross-link, are sensitive to UV light. The treatment of the CNBr peptides with UV light prior to Western blot destroys the pyridinium ring and releases CB9,7 which was part of the cross-linked larger peptide. This treatment resulted in immunostaining with E1E5 or E4A11 only in the regions of CB8 and CB9,7. The time course shows the disappearance of larger (cross-linked) peptides and the increase of staining of CB9,7 band. See FIGS. 2 and 3.

Figure 2:
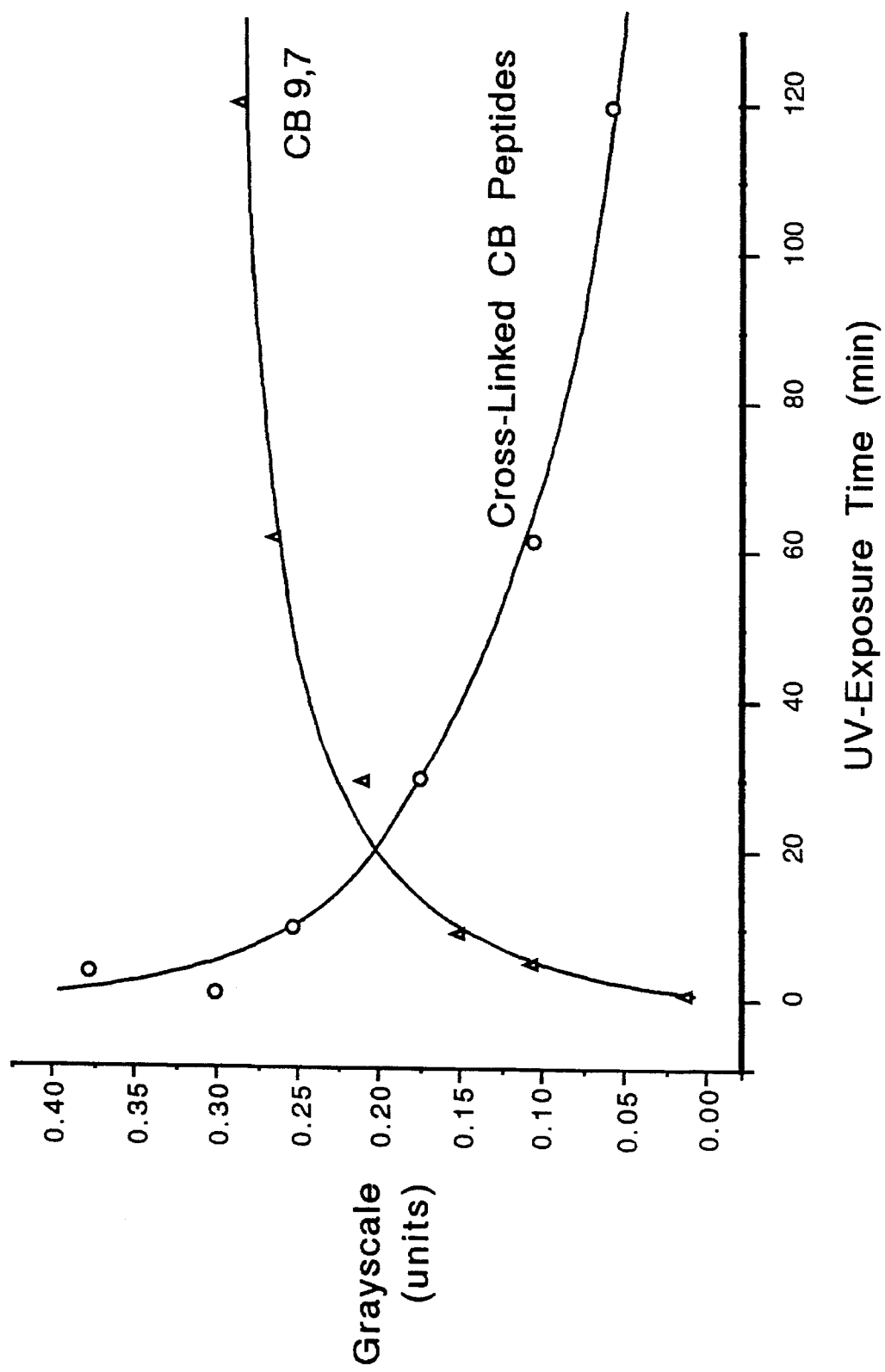
FIG. 2 is a graph showing the effect of UV light exposure on cross-linked CNBr peptides derived from rabbit articular cartilage.
Figure 3:
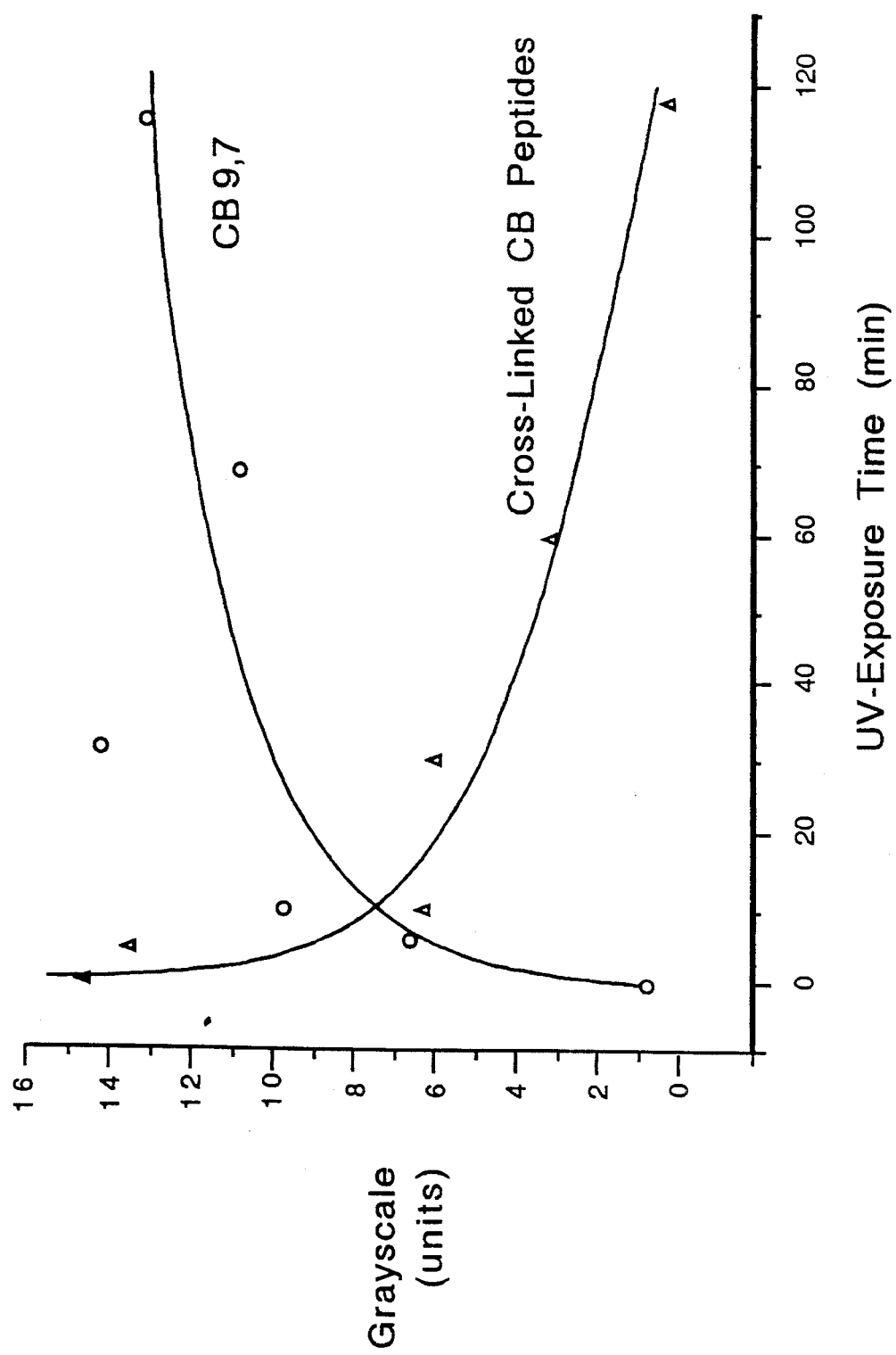
FIG. 3 is a graph showing the effect of UV light exposure on cross-linked CNBr peptides derived from collagen Type II purified from rat chondrosarcoma.

In the FIG. 2 experiment, rabbit articular CNBr peptides were dissolved in 0.5M HAc (5 mg/ml). The peptide solution was transferred into quartz cuvettes and exposed to UV light (254 nm). At different time points (0–120 minutes) an aliquot of 100 µl sample buffer and the peptides were analyzed by Western Blot employing the monoclonal antibodies E1E5. The stained membranes were scanned and analyzed using the Image Software on a Macintosh LC computer. The staining intensity in the stained bands were expressed as grayscale units. FIG. 3 is the result of a similar experiment in which cross-linked CNBr peptides derived from purified collagen Type II (rat chondrosarcoma) were used.

In Type II collagen the pyridinium cross-links contain as helical component either CB12 (M.W. -8,000) or CB9,7. See Wu, J. et al. Biochem. 23:1850 (1984), which is hereby incorporated by reference in its entirety. The monoclonal antibodies E1E5 and E4A11 are directed against the amino acid sequence which is in close location to the cross-linking pyridinium ring within the sequence of CB9,7. The antibodies do not react with CB12.

The binding of the monospecific monoclonal antibodies E1E5 and E4A11 to two CNBr peptides, CB8 and CB9,7, derived from collagen Type II led us to use the Mac-Vector program to search the protein bank for homologous amino acid sequences in the collagen Type II molecule. Searching the complete collagen Type II molecule (human) two respective sequences of 12 amino acids in CB8 and CB9,7 which are essentially identical were found: Gly-Phe-Gln-Gly-Leu-Asp-Gly-Pro-Hyp-Gly-Pro-Hyp-Gly SEQ. ID NO:3 and Gly-Leu-Gln-Gly-Leu-Hyp-Gly-Hyp-Hyp-Gly-Hyp-Ser-Gly. SEQ. ID NO:2 (Note that the 12-amino acid segment of CB9,7 is inferred from a DNA sequence encoding CB9,7 and Xaa stands for either Pro or Hyp.) Within the peptide 9,7, the sequence is close to the amino acid lysine which is part of the pyridinium cross-link with two other collagen Type II molecules.

The epitope for E1E5 is thus within these amino acids in the homologous sequence for the following reasons: First, this sequence is only found in CB8 and CB9,7 in Type II collagen molecule. Second, this sequence is in close proximity to the pyridinoline cross-link in CB9,7. Therefore, this part of the collagen Type II molecule is protected and present in natural occurring peptides in body fluids, cell cultures or organ cultures. Finally, searching the protein bank did not result in matches of this sequence with collagen types I, III or IV. This sequence is very unique to collagen Type II.

Immunoassays

The immunoassay method of the present invention is preferably based on modified enzyme immunoassays, e.g., inhibition ELISA, Western blots and slot or dot blot assays.

Depending upon the particular protocol employed, unlabeled or enzyme-labeled derivatives of monoclonal antibodies are used. In the case where specific monoclonal antibodies against the extracellular matrix protein or its peptides are not enzyme-labeled, a different detectable marker, for example, an enzyme-labeled antibody capable of binding to the monoclonal antibody, may be employed. Highly purified and characterized Type II collagen or its CNBr peptides are used as standards to calculate unknown concentrations. The collagen or collagen peptides in the sample to be quantified is either bound to solid phase or reacts with immobilized antibodies or is preincubated with specific antibodies to form an antigen-antibody complex.

To demonstrate how an immunoassay of this invention can be performed, the inhibition ELISA is described in detail below. First, purified extracellular matrix protein or its peptides is immobilized on a solid support. Any of the common supports used in immunoassays may be employed. Suitable solid supports include, for example, the inner walls of glass tubes and polystyrene based microtiter plates, or solid particles made from various materials such as polypropylene, polystyrene, polyethylene and glass. After preincubation of the sample with the monoclonal antibodies, the free antibodies not complexed with the antigen present in the sample solution bind to the immobilized protein. Any substances in the sample which do not bind during this incubation step are washed from the solid support. The solid support is then contacted with an enzyme-labeled second antibody which is capable of binding to the specific monoclonal antibody which is bound to the immobilized antigen. After separation of any unbound enzyme-labeled second antibody from the solid, the complex is incubated with an enzyme substrate capable of reacting with the enzyme of the enzyme-labeled antibody to produce a detectable reaction product. The product of the enzymatic reaction is then measured and correlated with values of a standard curve of known concentration of antigen. The amount of Type II collagen in the sample is calculated from the standard curve.

The immunoassay methods of the present invention can also be employed upon the particular protocol, unlabeled or radioactively labeled derivatives of monoclonal antibodies which bind collagen Type II antigens, either alone or in combination. In the case where the collagen Type II antigen binding monoclonal antibody is unlabeled, a different detectable marker, for example, a radiolabeled collagen II antigen derivative, may be employed. Any of the known modifications of radioimmunoassay ("RIA"), for example, homogeneous RIA, heterogeneous RIA, competitive RIA, and sandwich RIA may be employed.

The immunoassay method of the present invention may also be other known immunoassay methods, for example, fluorescent immunoassays using antibody conjugates or antigen conjugates of fluorescent substances such as fluorescein or rhodamine, and immunoassays employing an avidin biotin or strepavidin biotin detection system.

The antibodies may be bound to other solid matter such as glass beads with and without coating, Sepharose or Sephadex, or acrylic beads. Antigen bound to these antibodies may be detected on the beads or after elution on membranes (slot blot) or ELISA-plates (inhibition ELISA).

EXAMPLE 2

Using the four monoclonal antibodies (i.e., E1E5, E4A11, C4F6 and E6E3), assays were developed for quantitating native Type II collagen and CNBr peptides. These assays were performed as inhibition ELISAs where the antigen was allowed to complex with antibody present in excess in a preincubation step and the free antibody was then quantitated. Rennard et al., Anal. Biochem. 104:205 (1980). Assay conditions such as amount of the Type II collagen to be coated on the microtiter plates, the concentration of the monoclonal antibody to be employed in the inhibition ELISA, concentration of the goat anti-mouse HRPO conjugated antibodies and incubation times on the microtiter plates were optimized. Gosslau, et al. J. Immunol. Methods, 29:71 (1979). The optimal antigen coating concentration for Type II collagen was found to be 2 µg/ml for antibodies E6E3 and C4F6. For antibodies E1E5 and E4A11, the optimal coating concentration of Type II collagen CNBr peptides was found to be 0.5 µg/ml. The optimal antibody concentrations were determined for quantitating Type II collagen and CNBr peptides of Type II collagen and are listed in Table II.

TABLE II

Precision and Sensitivity Values of the Quantitative Immunoassays

| Antibody (Protein concentration)* | C4F6 (238.7 ng/ml) | E6E3 (32.9 ng/ml) | E1E5 (9.28 ng/ml) | E4A11 (16.3 ng/ml) |
|---|---|---|---|---|
| Antigen | native | native | CNBr | CNBr |
| Antigen concentration ng/ml** | 194.6 | 194.6 | 191.0 | 191.0 |
| Within assay variance (Sw) | 0.010 | 0.006 | 0.003 | 0.004 |
| Precision % CVw | 4.063 | 0.810 | 0.941 | 1.366 |
| Between assay variance (Sb) | 0.023 | 0.047 | 0.027 | 0.009 |
| Reproducibility % CVb | 9.359 | 5.720 | 7.048 | 2.733 |
| Minimal detectable concentration | 6.45 ng/ml | 22.7 ng/ml | 18.3 ng/ml | 34.0 ng/ml |

*The antibody concentration employed in the Elisas were expressed per unit of protein.
**Type II collagen concentrations were corrected by hydroxyproline analysis.

Figure 4A:
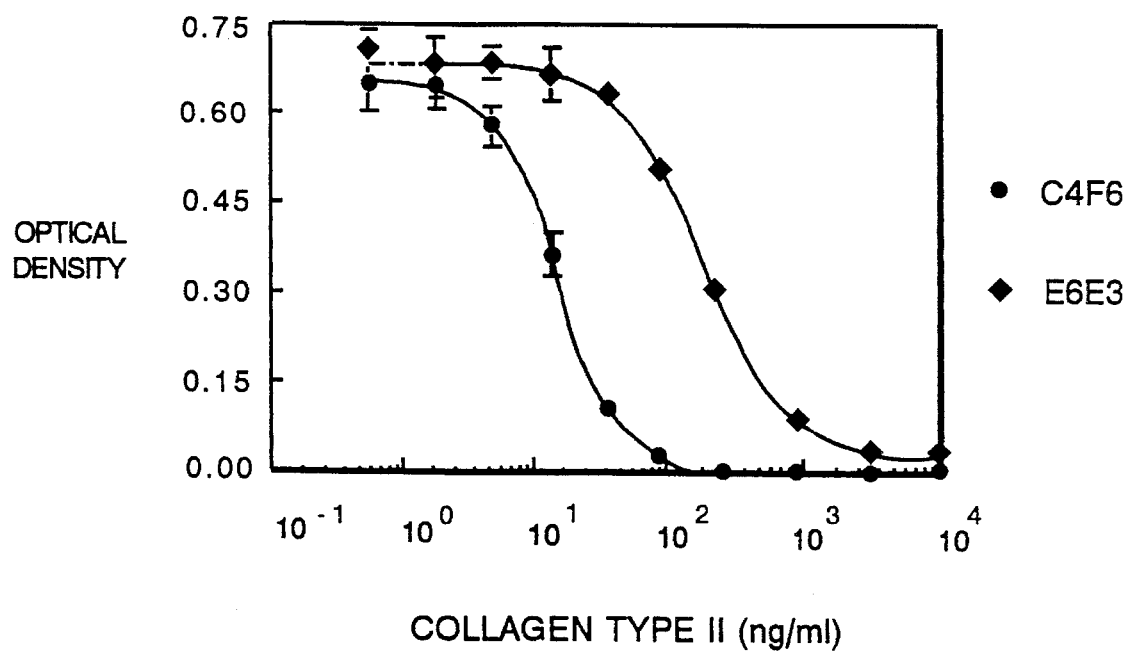
FIG. 4 is a set of graphs showing standard inhibition ELISA curves with Type II collagen monospecific antibodies.

Inhibition ELISA curves generated utilizing the optimal assay conditions described above are shown in FIG. 4. Antibody samples were incubated with increasing amounts of Type II collagen (FIG. 4A) or Type II collagen derived cyanogen bromide peptides (FIG. 4B) in Dulbecco's modified Eagle's medium with 10% FCS at room temperature for 24 hours. The mixtures were then transferred to microtiter plates coated with the same antigen employed in the incubation step, at a predetermined optimal concentration. The binding of the antibodies to the solid phase antigen was measured by ELISA and the optical density values were read at 450 nm.

Figure 5A:
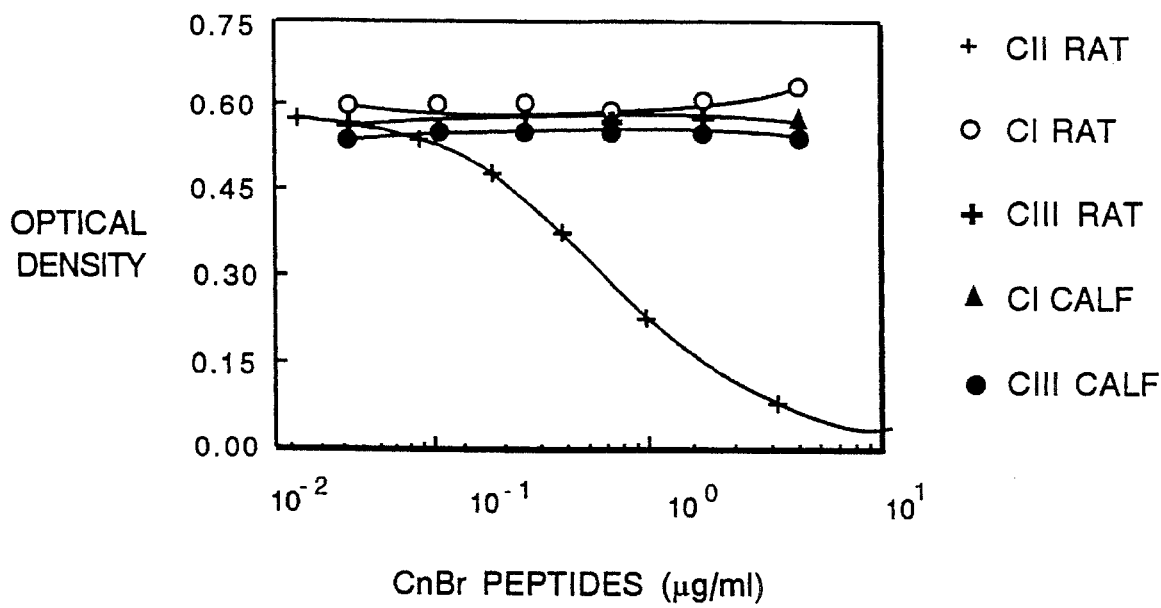
FIG. 5 is a set of graphs showing specificity of E1E5 and E4A11 by inhibition ELISA.
Figure 5B:
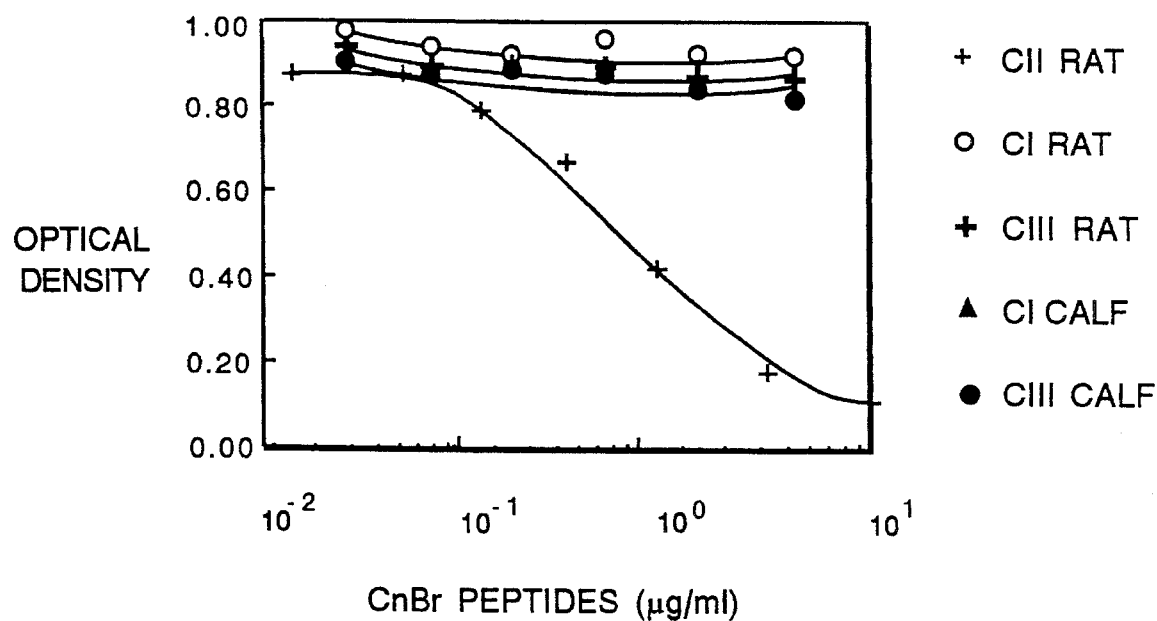

The sensitivities of the assays developed with these four antibodies expressed as IC-50 values are listed in Table I. Assays employing antibodies C4F6 and E6E3 could quantitate nanogram levels of native Type II collagen but did not detect CNBr peptides. On the other hand, assays employing E1E5 or E4A11 could easily quantitate low amounts of CNBr peptides or Type II collagen in denatured configuration. The specificity for Type II collagen CNBr peptides is further demonstrated by the fact that the inhibition ELISAs were not influenced by CNBr peptides of collagen types I or III (FIGS. 5A and 5B). Also shown in Table I are the Kd values of C4F6, E6E3, E1E5 and E4A11, which were calculated according to the method of Friguet. See Friguet, B. et al. J. Immunol. Methods 77:305 (1985), hereby incorporated by reference.

The recovery was estimated by adding known concentrations of Type II collagen or CNBr peptides to culture medium to be quantified at different times. The antigen concentrations were selected within the slope region of the standard curve and the inhibition assay was performed six different times in triplicates for each concentration selected. The collagen content of the standards was determined by measuring hydroxyproline content. The within-assay variance (precision) and between-assay variance (reproducibility) were then estimated according to the method of Rodbard [Rodbard D., Clin. Chem. 20:1255 (1971)]. The percent within-assay variance (CVw%) and between-assay variance (CVb%) calculated were found to be less than 10% (Table II). The minimal detectable concentration was calculated at the O.D. values three standard deviations below that of control values. For the antibodies E6E3, C4F6, E1E5 and E4All, the minimum detectable concentrations were 22.7 ng/ml, 6.4 ng/ml, 18.3 ng/ml and 34 ng/ml (Table II).

EXAMPLE 3

Chondrocyte cultures have been used extensively as a model to study proteoglycan and Type II collagen synthesis. To demonstrate the applicability of the Type II collagen immunoassays, primary cultures of Swarm rat chondrosarcoma were utilized.

Chondrocytes were isolated from the propagated tumor using collagenase treatment and then cultured in confluent monolayers and initially plated at $5 \times 10^5$ cells/well of a 24 well plate (Corning 25801) and allowed to stabilize in Dulbecco's modified Eagles medium containing 20% fetal calf serum. Then the medium was completely changed and fetal calf serum concentration was maintained at 10% throughout the rest of the experiment. Both cells and medium were harvested on days 2, 4, and 5 and protease inhibitors (10 mM ethylene diaminetetraacetic acid and 1 mM phenyl methyl sulfonyl fluoride) were added. Type II collagen in the cell layer was extracted in 1M NaCl 0.05M Tris buffer at pH 7.4 and its concentration in both cell layer and medium was estimated. The levels of Type II collagen were quantitated in both the media and cell layers using the assay developed with monoclonal antibody C4F6. Proteoglycan content in the medium and cell layer was measured according to the method of Farndale (Farndale et al. Connective Tissue Research 9:247 (1982) and the results were expressed per mg DNA as determined by Hinegardner (Hinegardner, J. Immunol. Methods, 83:379 (1971). More specifically, the chondrocytes were isolated from propagated rat chondrosarcoma and cultured in confluent monolayers in 24 well plates (Corning 25801). Both the medium and cells were harvested at days 0, 2, 4 and 5 and protease inhibitors were immediately added to prevent any degradation. The Type II collagen and proteoglycan content were then determined in both cell layers and medium. Values represent mean ± S.D.

Figure 6A:
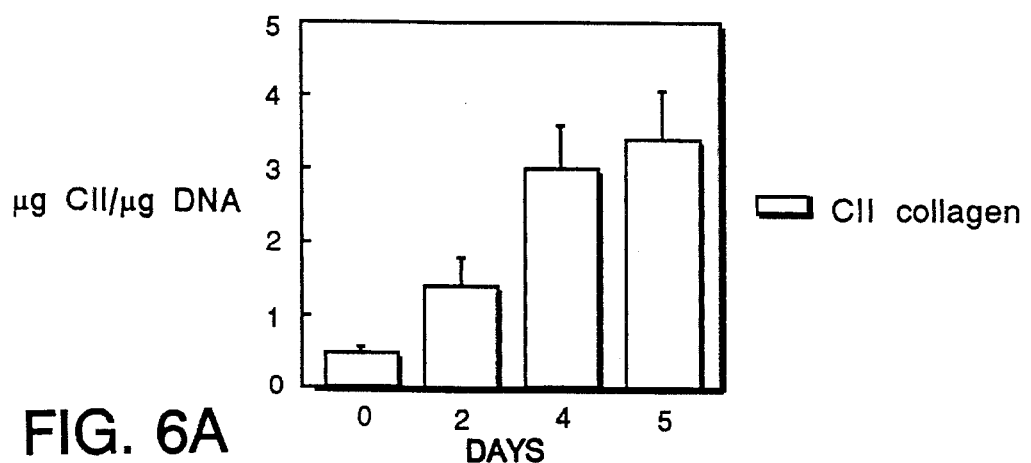
FIG. 6 is a set of graphs showing production of Type II collagen and proteoglycan by rat chondrosarcoma cultures.
Figure 6B:
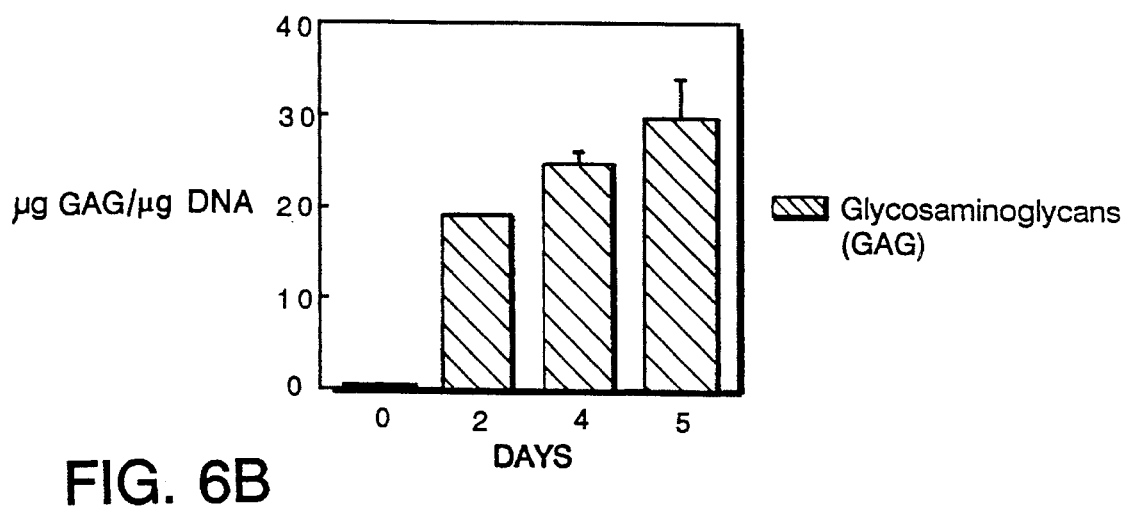

As seen in FIG. 6, there was a time dependent increase in Type II collagen and proteoglycan content over a four day period. Type II collagen was increased 7.1 fold by day 4 and proteoglycan increased by 31.3 fold.

The chondrosarcoma culture system combined with ELISA for Type II collagen content can be used for screening of antiarthritic drugs. In this system we can quantitate the effects of compounds that stimulate or inhibit Type II collagen synthesis. A number of nonsteroidal anti-inflammatory drugs have been shown to suppress proteoglycan and/or collagen synthesis in chondrocyte cultures. Fujii et al. Seminars in Arthritis and Rheumatism 18:16 (1989); Brandt, K. D., American Journal of Medicine 83:29 (1987). We tested the effect of the nonsteroidal agent indomethacin on Type II collagen and proteoglycan production in the chondrosarcoma culture system.

More specifically, chondrocytes were isolated from the propagated tumor of the Swarm rat chondrosarcoma using collagenase treatment. The isolated cells were plated at a density $10^6$ cells/well in a 24 well plate (Corning 25801). Cells were allowed to stabilize for 18 hours in Dulbecco's modified Eagle's medium containing 20% FCS. After the stabilization period the medium was changed and media containing 10% FCS, 50 µg/ml B-aminoproprionitrile together with indomethacin at the concentrations indicated. At the end of four days the amount of collagen Type II and proteoglycan were quantitated in the cell medium and cell layer extracts.

Figure 7A:
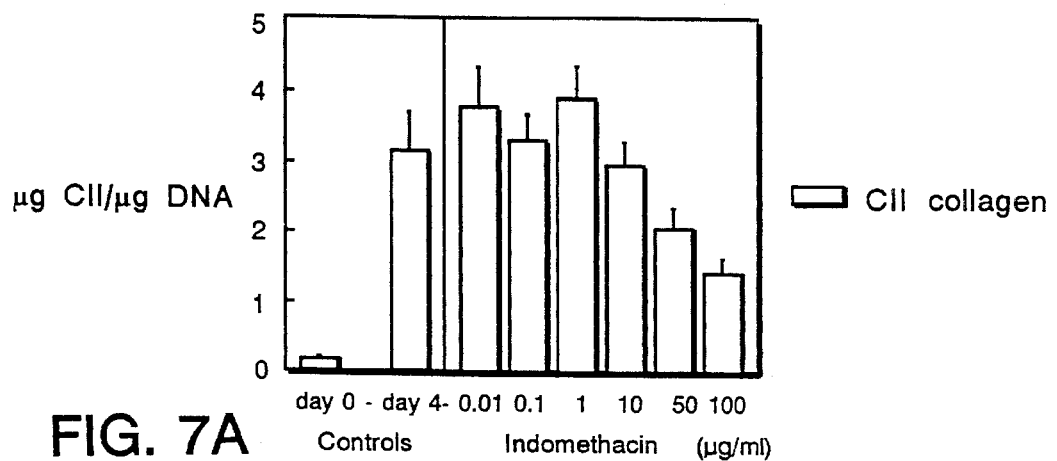
FIG. 7 is a set of graphs showing effect of indomethacin on Type II collagen and proteoglycan production by chondrosarcoma cultures.
Figure 7B:
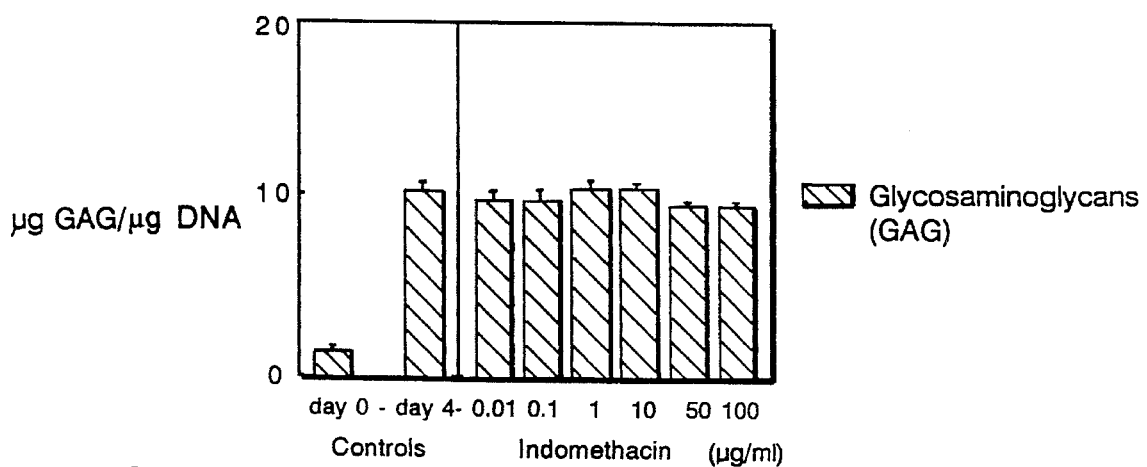

As seen in FIG. 7, values represent mean ±standard deviation for 6 replicates. Asterisk indicates a value significantly different from day 4 controls at a level of $p<0.01$ using one way ANOVA. With increasing of the dose of indomethacin, the synthesis of Type II collagen was decreased. No effect of indomethacin on proteoglycan production was seen. Type II collagen synthesis appears to be more sensitive to the effects of indomethacin than the proteoglycan synthesis.

EXAMPLE 4

The ELISA utilizing C4F6 or E6E3 can be used to quantitate intact helical Type II collagen while E1E5 or E4A11 can be used for denatured or degraded Type II collagen quantification. These assays can be employed in the same samples with no cross interference. Examples of the specificity is shown in FIGS. 8 and 9.

Figure 8:
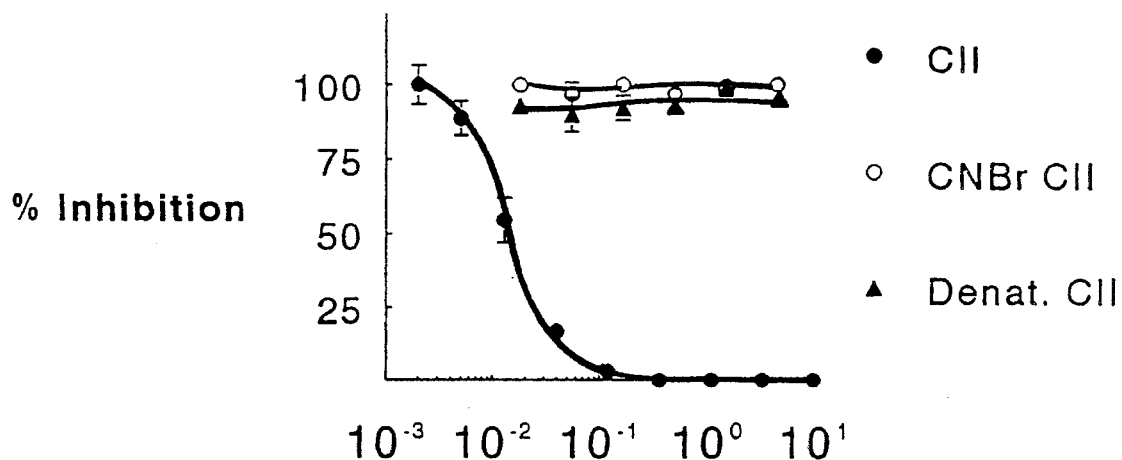
FIG. 8 is a graph showing results from inhibition ELISA using antibody C4F6.

In the FIG. 8 experiment, antibody C4F6 samples were incubated with increasing amounts of Type II collagen, Type II collagen peptides or heat denatured Type II collagen in Dulbecco's modified Eagle's medium with 10% FCS at 4° C. for 24 hours. The mixtures were then transferred to microtiter plates coated with Type II collagen. The binding of the antibodies to the solid phase antigen was measured by ELISA and the optical density values were read at 450 nm.

Figure 9:
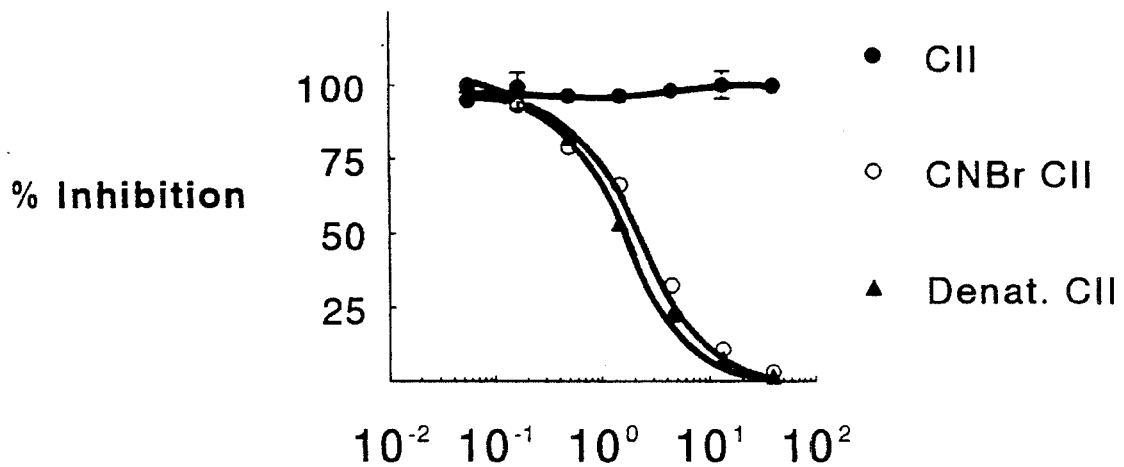
FIG. 9 is a graph showing results from inhibition ELISA using antibody E1E5.

In the FIG. 9 experiment, antibody E1E5 samples were incubated with increasing amounts of Type II collagen, Type II collagen cyanogen derived peptides or heat denatured Type II collagen in PBS pH 7.4 containing 0.05% Tween 20 and 1% bovine serum albumin. Samples were incubated at 4° C. for 24 hours and the mixtures were then transferred to microtiter plates coated with Type II collagen derived cyanogen bromide peptides. The binding of the antibodies to the solid phase antigen was measured by ELISA and the optical density values were read at 450 nm.

As shown in FIG. 8, the ELISA for native Type II collagen employing antibody C4F6 was not interfered by denatured Type II collagen (Denat. CII) or its peptides (CNBr CII). On the other hand, Type II collagen peptides or denatured Type II collagen showed no interference with native Type II collagen by the ELISA employing antibody E1E5 (FIG. 9).

Figure 10A:
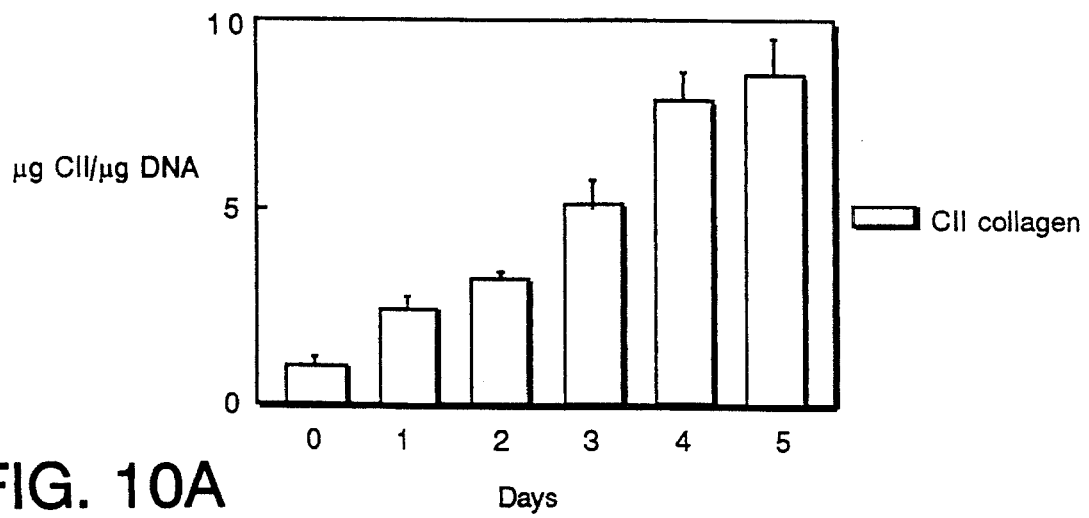
FIG. 10 is a set of graphs showing production of Type II collagen and Type II collagen peptides by rat chondrosarcoma cultures.
Figure 10B:
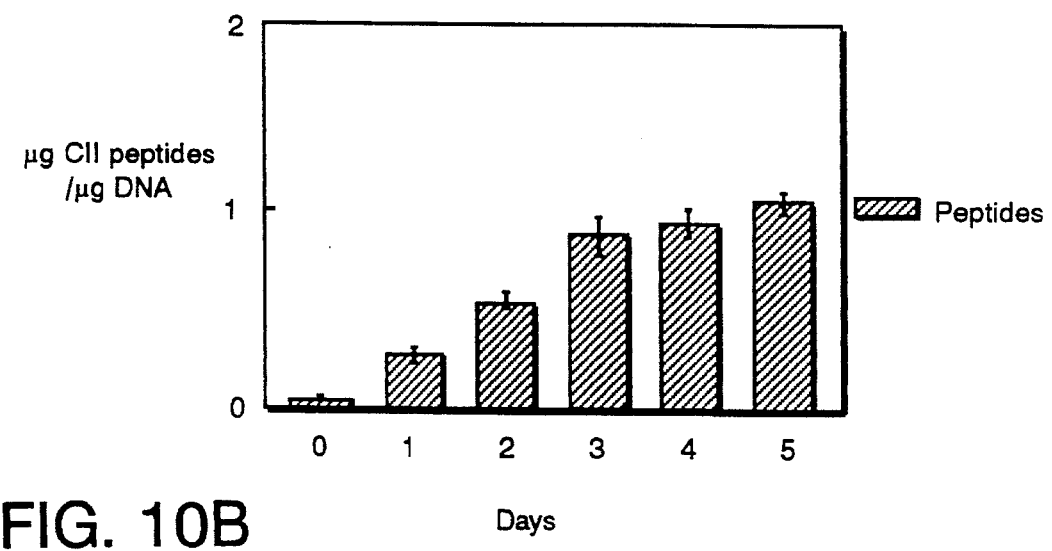

These assays can be applied to quantitate Type II collagen synthesis and degradation in the same culture sample. In the FIG. 10 experiment, chondrocytes were isolated from the propagated tumor and cultured in confluent monolayers in 24 well plates. Both medium and cells were harvested at days 0, 1, 2, 3, 4 and 5 and protease inhibitors were added to prevent degradation. Type II collagen and Type II collagen derived peptides were then determined by ELISA in both cell layers and medium and were expressed per µg DNA. Values in FIG. 10 represent mean ±S.D., n=6. Over a 4 day period samples taken from the rat chondrosarcoma chondrocyte culture system showed a linear increase of collagen Type II and collagen Type II derived peptides content (FIG. 10).

Figure 11A:
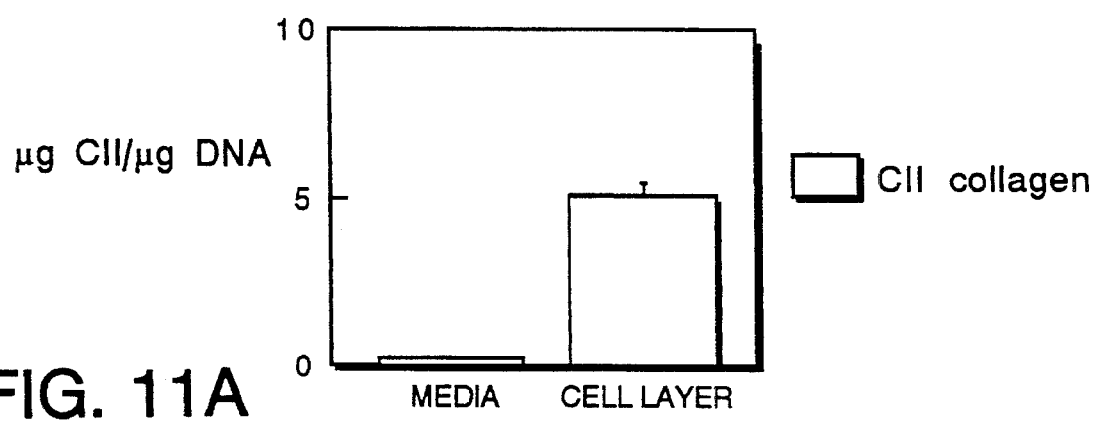
FIG. 11 is a set of graphs showing distribution of Type II collagen and Type II collagen peptides in rat chondrosarcoma cultures.
Figure 11B:
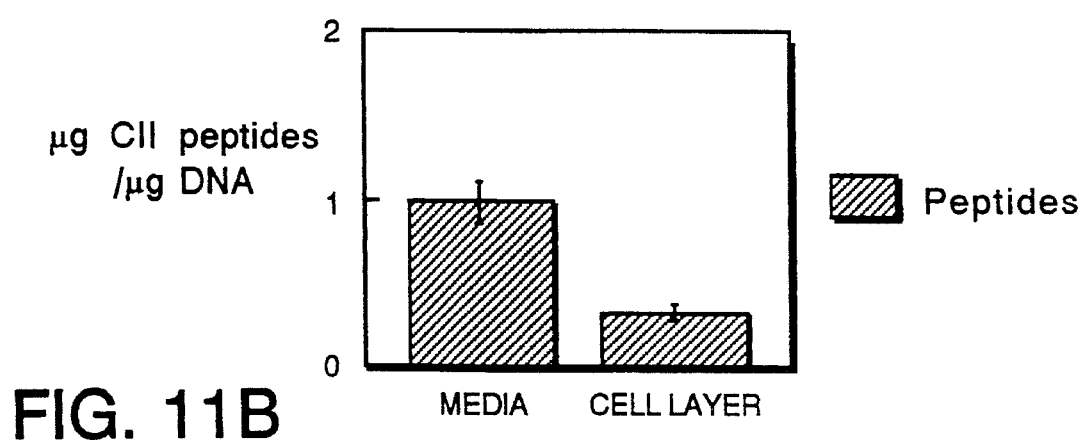

In the FIG. 11 experiment, rat chondrosarcoma chondrocytes were cultured as described above. At the end of four days, both the medium and cells were harvested and protease inhibitors were added to prevent degradation. Type II collagen and Type II collagen peptides were determined by ELISA in both cell layers and medium and were expressed per µg of DNA. The amount of Type II collagen and Type II collagen peptides in the media and cell layer at day 4 is shown in FIG. 11, values representing mean ±S.D., n=6. In this culture system, the majority of the native collagen Type II was found associated with the cell layer while the Type II collagen derived peptides were found in the media.

Figure 12A:
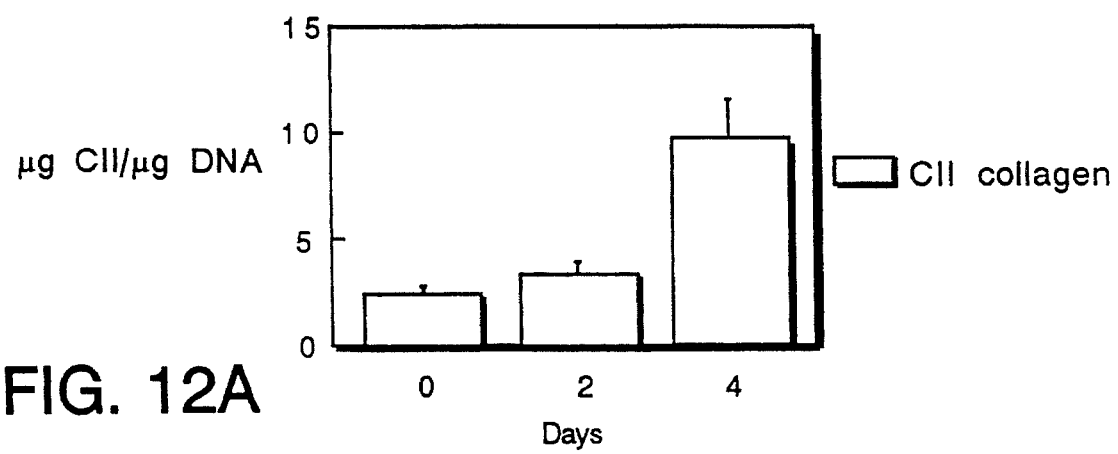
FIG. 12 is a set of graphs showing production of Type II collagen and Type II collagen peptides by rabbit chondrocyte cultures.
Figure 12B:
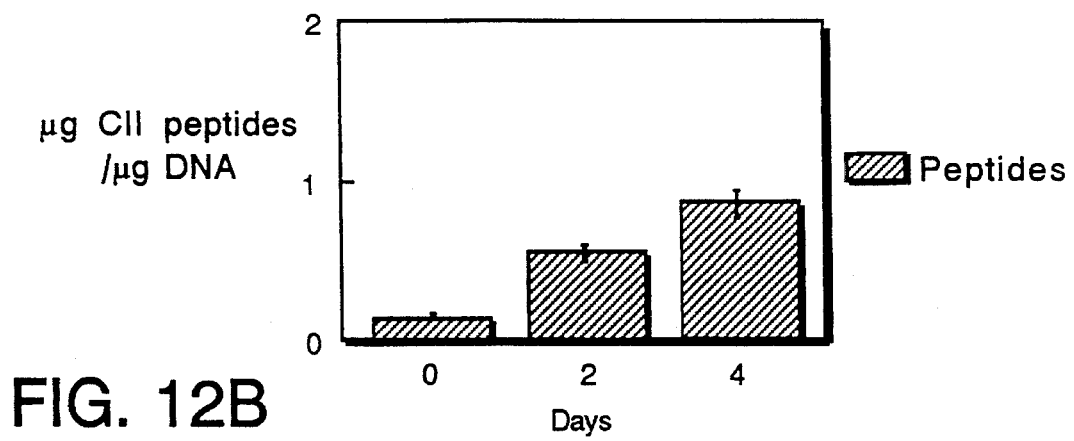

These assays can be applied to other culture systems using rat, rabbit, calf, or human chondrocytes. An example of data generated with cultured rabbit chondrocytes is shown in FIG. 12. Rabbit articular chondrocytes were isolated using collagenase digestion. They were placed into culture using similar culture conditions as the rat chondrosarcoma cells in a T-75 flask. When the cells were confluent, the media was changed to Dulbecco's modified Eagle's medium containing 10% FCS and 50 µg/ml ascorbic acid and 50 µg/ml B-aminoproprionitrile. At the times indicated cell layers and media were harvested and protease inhibitors added. Type II collagen and Type II collagen derived peptide were then determined in medium and cell layer extracts by ELISA and expressed per µg of DNA. Values represent mean ±S.D., n=6.

As seen in FIG. 12 there is a time dependent increase in collagen Type II and collagen Type II derived peptides in cell layer and medium combined.

Figure 13A:
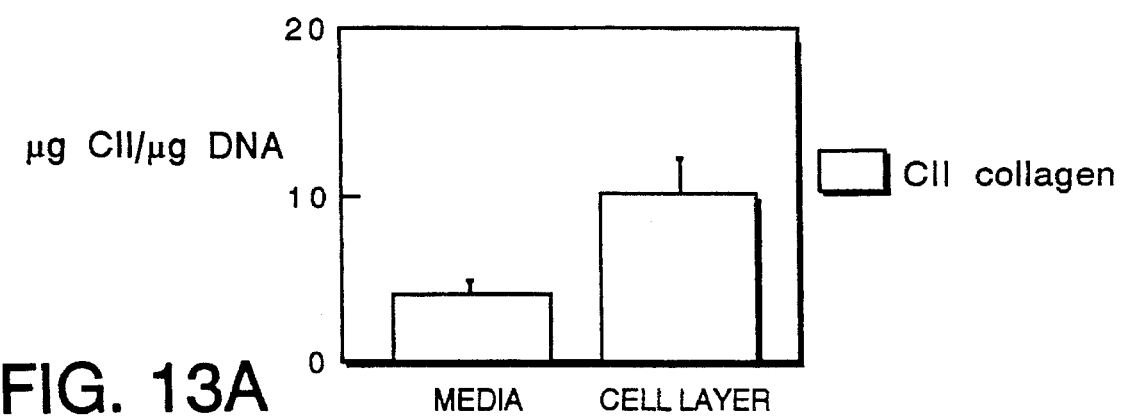
FIG. 13 is a set of graphs showing distribution of Type II collagen and Type II collagen peptides in rabbit chondrocyte cultures.
Figure 13B:
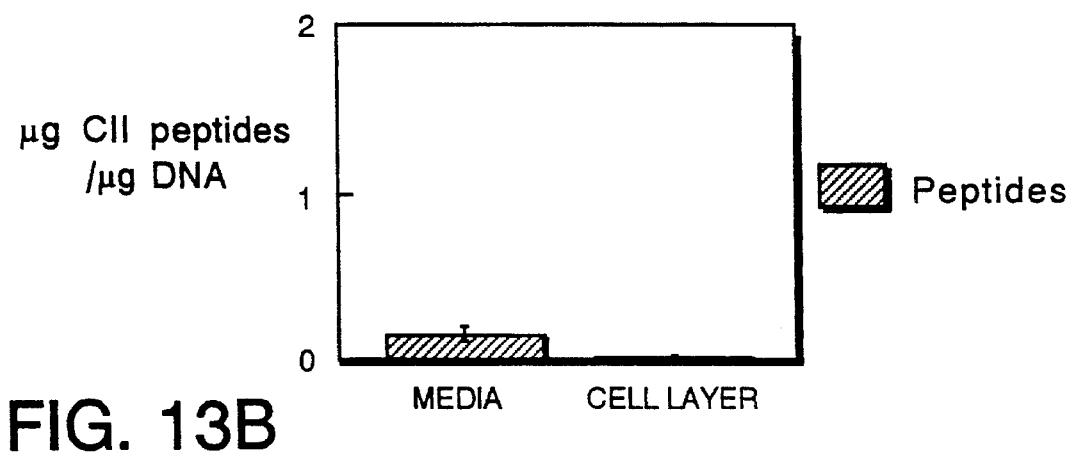

The distribution of collagen Type II and its peptides at day 4 in culture in medium or cell layer of collagen Type II separately was studied. More specifically, Rabbit articular chondrocytes were cultured as previously described. At the end of four days following the final media change, both the medium and cells were harvested. Type II collagen and Type II collagen derived peptides were determined by ELISA in both cell layers and medium, and were expressed per µg of DNA. Values represent mean ±S.D., n=6. As shown in FIG. 13, in the rat chondrosarcoma system, the higher quantity of native Type II collagen was found in the cell layer while the majority of the Type II collagen peptides was found in the media.

There was a large difference between the proportion of peptide to native form in the rat and rabbit culture systems. On day 4, in the rat chondrosarcoma chondrocyte culture, approximately 33% of the total Type II collagen molecules was in a non-helical peptide form while in the rabbit articular chondrocyte cultures only 1 to 2%.

The two assays for native collagen Type II and for denatured or peptides of collagen Type II allow the quantitation of synthesis and degradation of Type II collagen in chondrocyte or cartilage explant cultures. They provide methodologies by which the degradation of Type II collagen can be studied and also allow the identification of potential antiarthritic compounds which alter the synthesis or degradation of Type II collagen. Two examples are provided utilizing the rat chondrosarcoma chondrocyte culture system.

Figure 14A:
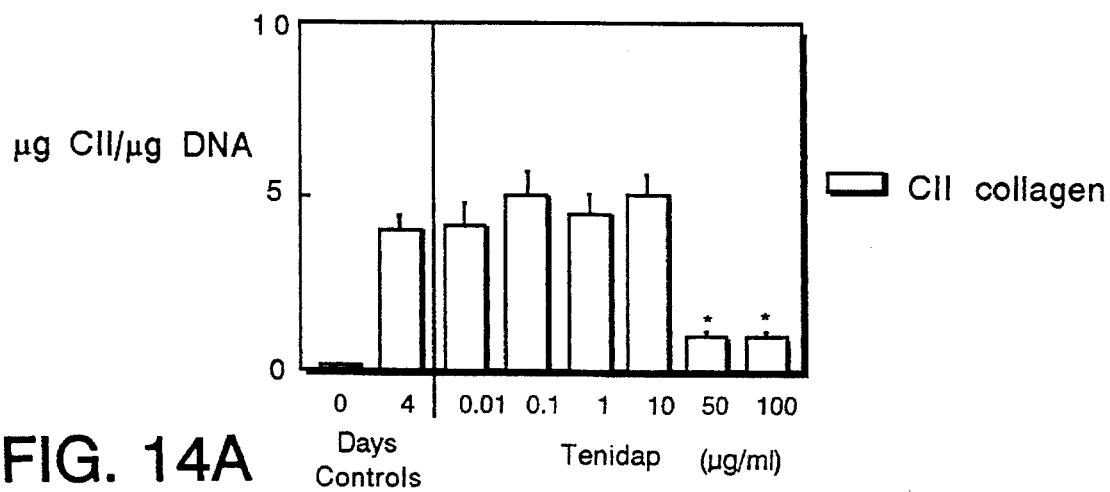
FIG. 14 is a set of graphs showing effect of tenidap on Type II collagen and Type II collagen peptides production by chondrosarcoma cultures.
Figure 14B:
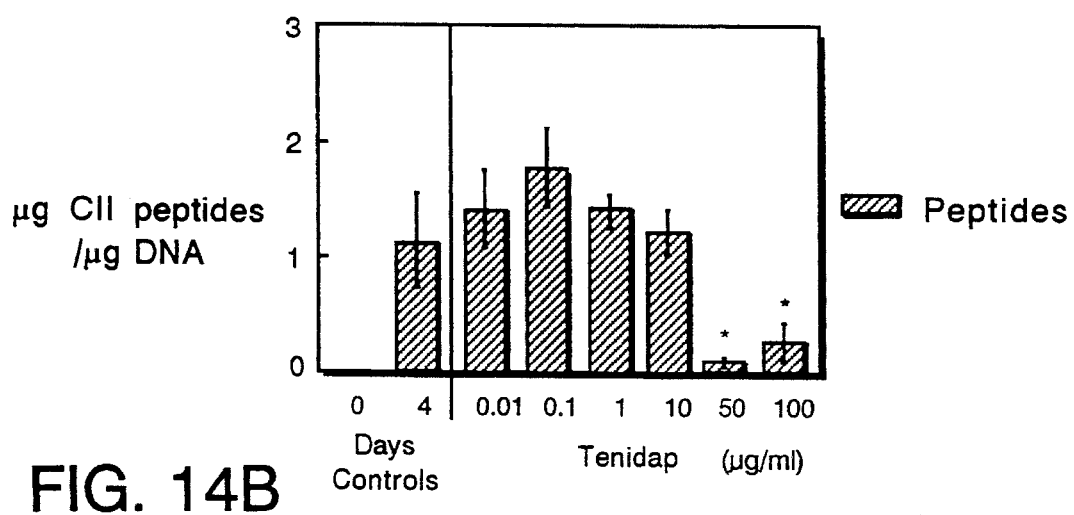
Figure 15A:
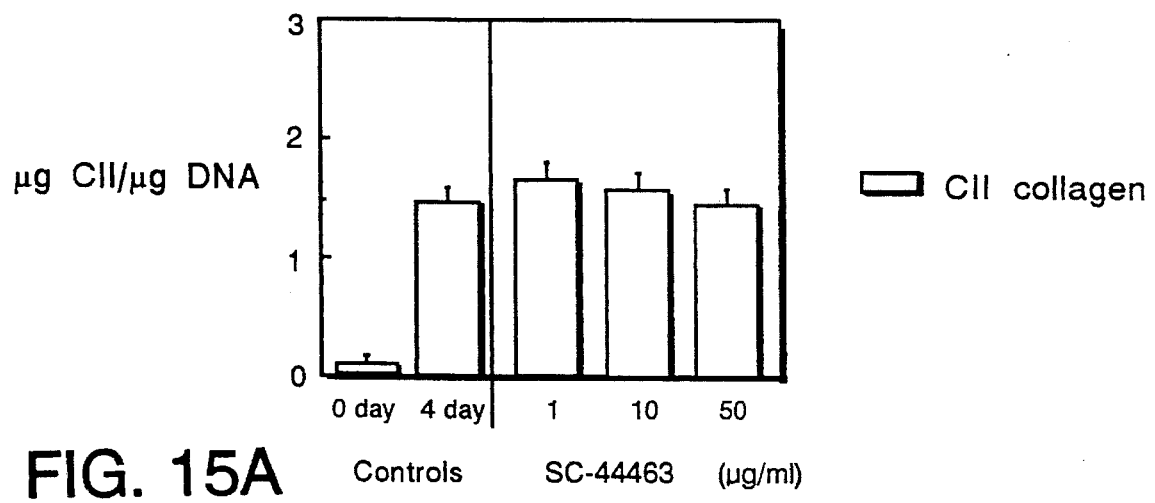
FIG. 15 is a set of graphs showing effect of the collagenase inhibitor, SC-44463, on Type II collagen and Type II collagen derived peptide production by chondrosarcoma cultures.
Figure 15B:
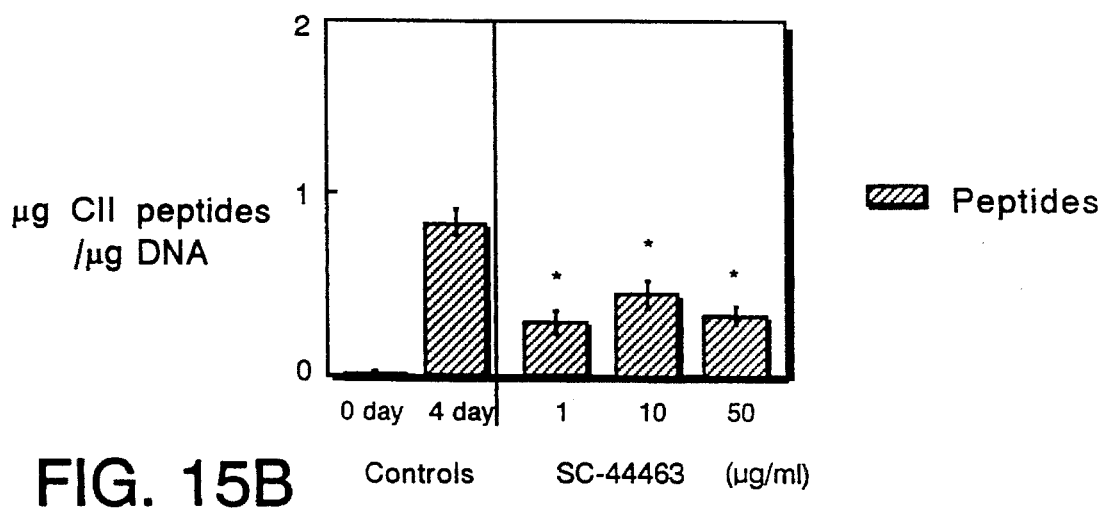

The FIG. 14 experiment studied the effect of Tenidap, a novel anti-infammatory compound, is shown. Chondrocytes were isolated from the propagated rat chondrosarcoma and cultured as previously described. After the initial stabilization period the medium was changed and medium containing 10% FCS, 50 µg/ml ascorbic acid, and 50 µg/ml B-aminoproprionitrile together with tenidap at the concentrations indicated. At the end of four days the amount of Type II collagen and Type II collagen derived peptides were quantitated by ELISA. Values represent mean ±S.D. for 8 replicates. Asterisks indicate values significantly different from day 4 controls at the level of $p<0.01$ using one way ANOVA. As shown in FIG. 14, at concentration of 50 and 100 mg/ml, there was a dramatic drop in both Type II collagen and Type II collagen peptide concentrations as an expression of inhibition of collagen Type II synthesis. Other compounds, however, may specifically inhibit the production of Type II collagen peptides. In the FIG. 15 experiment, chondrocytes were isolated from the propagated rat chondrosarcoma and cultured as previously described. After the initial stabilization period the medium was changed and medium containing 10% FCS, 50 µg/ml ascorbic acid, 50 µg/ml B-aminoproprionitrile together with SC-44463 at the concentrations indicated. At the end of day 4, the amount of Type II collagen and Type II collagen peptides were quantitated by ELISA. Values represent mean ± S.D. for 6 replicates. Asterisks indicate values significantly different from day 4 controls at the level of $p<0.01$ using one way ANOVA. When the collagenase inhibitor SC-44463 was added there was an inhibition of collagen Type II degradation expressed by lower concentration of peptides with no effect on Type II collagen levels (FIG. 15). Thus, the Type II peptide assay can be used to evaluate compounds that may prevent the degradation of Type II collagen.

The degradation of articular cartilage has been associated with increased activities of matrix metalloproteinases including the enzyme collagenase. A number of cytokine mediators, including Interleukin-1 (Il-1), have been shown to stimulate the release of proteases such as collagenase from cartilage. In addition Il-1 inhibits the synthesis of Type II collagen by decreasing mRNA levels. The assay for Type II and Type II collagen peptides would be of great value to examine the mechanism by which cytokines such as Il-1 induce cartilage breakdown and for the screening of compounds which inhibit this breakdown process. To illustrate this point, Il-1 was added to rabbit chondrocyte cultures (Table III). After four days the cells and media were harvested and collagen Type II and collagen Type II peptides were measured. A significant decrease in intact collagen Type II and a increase in the peptide form of collagen Type II was seen at 1 ng/ml and 10 ng/ml concentrations of Il-1. The ratio of collagen Type II derived peptides to intact collagen Type II, was more than two fold as the result of Il-1 treatment.

TABLE III

Effect of Interleukin-1 on Collagen Type II and Collagen Type II Derived Peptides on Rabbit Articular Chondrocytes*

|  | CII (μg CII/μgDNA) | CII Peptides (μg pep./μg DNA) | CII Peptides/CII % |
|---|---|---|---|
| Control | 13.5 ± 2.1 | 0.18 ± .05 | 1.3 |
| Il-1 Treated | 7.7 ± 1.2 | 0.24 ± .06 | 3.1 |

*Cells were treated with 1 ng/ml of IL-1.

The amount of collagen Type II peptides is dependent not only on the activity of the enzymes that break down collagen, but also on the amount of collagen that is available to these enzymes as substrate. In the chondrocyte culture system there is a net increase in collagen Type II over time. At a constant concentration of collagen degrading enzymes, an increase in collagen Type II peptides parallels the increase of collagen Type II over time. If collagen Type II synthesis is blocked, no increase in collagen Type II or collagen Type II derived peptides would be seen after four days of culture in comparison to untreated controls. This result was seen when Tenidap was tested in the rat chondrosarcoma chondrocyte culture system (FIG. 14). It is therefore necessary in culture experiments to quantitate both the collagen Type II and its peptides.

A different situation exists when using explant cultures. In this technique cartilage tissue is isolated and dissected into small fragments and placed into culture medium. A large amount of insoluble matrix containing Type II collagen surrounds the chondrocytes and is available for the matrix degrading enzymes. Over time, matrix components, specifically proteoglycan are lost into the media leaving an insoluble collagen framework. If Il-1 is added, the collagen matrix is degraded by the induced metalloproteinases and fragments are released into the surrounding culture medium. These fragments would be then detectable by the collagen Type II peptide assay. Unlike the chondrocyte culture system, there is a large amount of preformed Type II collagen available for degradation. Thus, in this system, the amount of collagen Type II peptides generated is not dependent upon collagen Type II synthesis. Cartilage explant cultures which respond well to Il-1, such as the bovine nasal septum cultures, are well suited for this type of work. In a typical bovine nasal cartilage explant culture, cartilage fragments are explanted into serum free culture medium and Il-1 is added. Culture medium is changed weekly. After the first week much of the proteoglycan from the explant matrix is released into the medium. In the third week the majority of the collagen is degraded and released into the media in cultures treated with Il-1. The amount of degraded Type II collagen can be quantitated using the CII peptide assay on the media.

EXAMPLE 5

Figure 16:
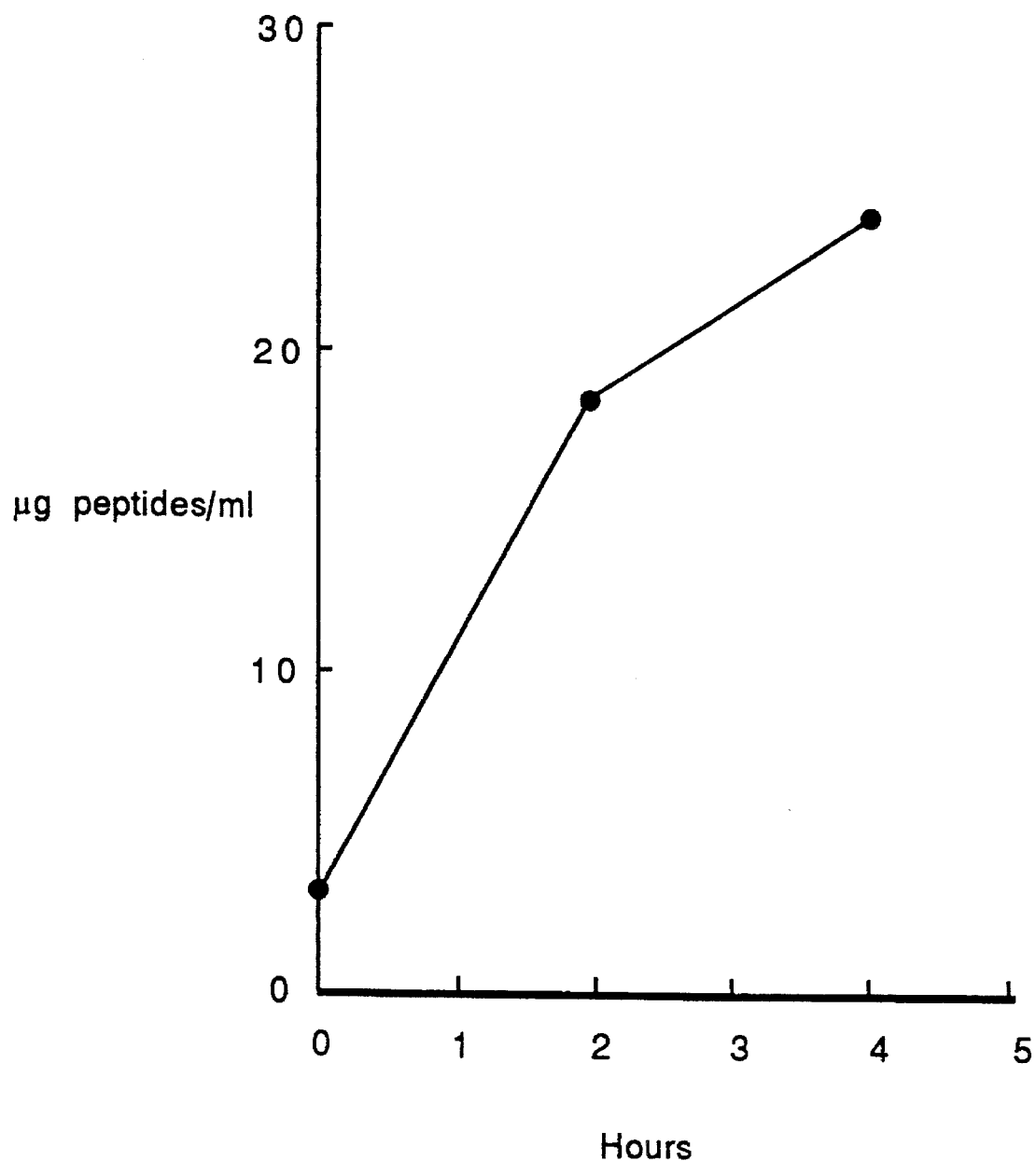
FIG. 16 is a graph showing in vitro generation of CII peptides by purified neutrophil collagenase from Type II collagen.

The native collagen Type II assay and the collagen Type II peptide assay can be used to determine collagenolytic activity in vitro. Mammalian collagenase cleaves the collagen Type II molecule in the region of CB10, causing a three-quarter/one-quarter split. This cleavage allows the unwinding of the triple helix at temperatures of 35° C. or higher. Bacterial collagenase cleaves collagen Type II molecules into small nonhelical peptides. Native collagen Type II is stable at 35° C. If native collagen is incubated with collagenase at 35° C., the collagen is degraded and the helix unwinds. The resulting fragments can be quantified with the collagen Type II peptide assay. This is illustrated in FIG. 16. Type II collagen (100 μg/ml) was incubated in collagenase buffer together with purified neutrophil collagenase which was activated by 0.5 mM 4aminophenyl mercuric acetate (25 μl) in 0.05M Tris HCl, 50 mM $CaCl_2$, 0.5M NaCl pH 7.4 (500 μl) at 35° C. Samples were removed at the times indicated and EDTA was added to stop the reaction. The Type II collagen peptide assay (inhibition ELISA) was then performed. At the times indicated, the reaction was stopped with EDTA and assayed for CII peptides. As can be seen, there was a time-dependent releasing of CII peptides. This assay for collagenase activity has advantages over other collagenase assays in that it does not use radioactivity and that it is adaptable to a large number of samples. Note that at the same time, the decrease of native collagen can also be measured with the native collagen Type II assay using C4F6 or E6E3, if desired.

EXAMPLE 6

Peptides derived from Type II collagen can be quantified in serum samples using monoclonal antibodies E1E5 in a slot blot assay. The serum samples can be prepared by trichloroacetic acid precipitation which removes most of the serum proteins and leaves collagen peptides in solution. The low pH during this procedure will disrupt any antibody-antigen complex which might involve collagen peptides and will release these peptides in free form into the supernatant for analysis.

To study sera from rabbits (White New Zealand) with surgically induced osteoarthritis (Hulth Model) at different time points after surgery, aliquots of serum samples were treated with cold TCA (final concentration 4%) and chilled on ice for thirty minutes after which they were centrifuged and the supernatant was removed. The supernatant was adjusted with NaOH to pH 7–8 and an aliquot was applied to a nitrocellulose membrane in a Milliblot apparatus.

Control sera with and without added collagen Type II CNBr peptides (CII peptides) were treated identically to the samples. For comparison of the amount of CII peptides present in the serum, a standard curve containing CII peptides in Tris buffered saline (TBS) or phosphate buffered saline (PBS) was applied to each membrane.

The membrane was incubated overnight at 8° C. Then the dry Milliblot slots were rinsed twice with Tris buffered saline containing TWEEN-20 (TBS-T). The membrane was removed from the apparatus, placed in a pan containing 50 ml TBS-T and gently agitated for 10 minutes. The washed membrane was blocked in 5% nonfat milk in TBS at room temperature for 45 minutes. After washing the membrane four times in TBS-T it was incubated with the first antibody (E1E5) for 2 hours at room temperature, then washed three times in TBS-T, and incubated for 1½ hours with peroxidase labeled IgG. Finally the membrane was washed three times with TBS-T, twice with TBS, and the substrate, hydrogen peroxide and DAB-CN, i.e., 3,3'-diaminobenzidine (2 mg/ml) with 4-chloro-1-naphthol (6 mg/ml), in citrate-phosphate buffer, pH 7.6 was added for development of color.

Figure 17:
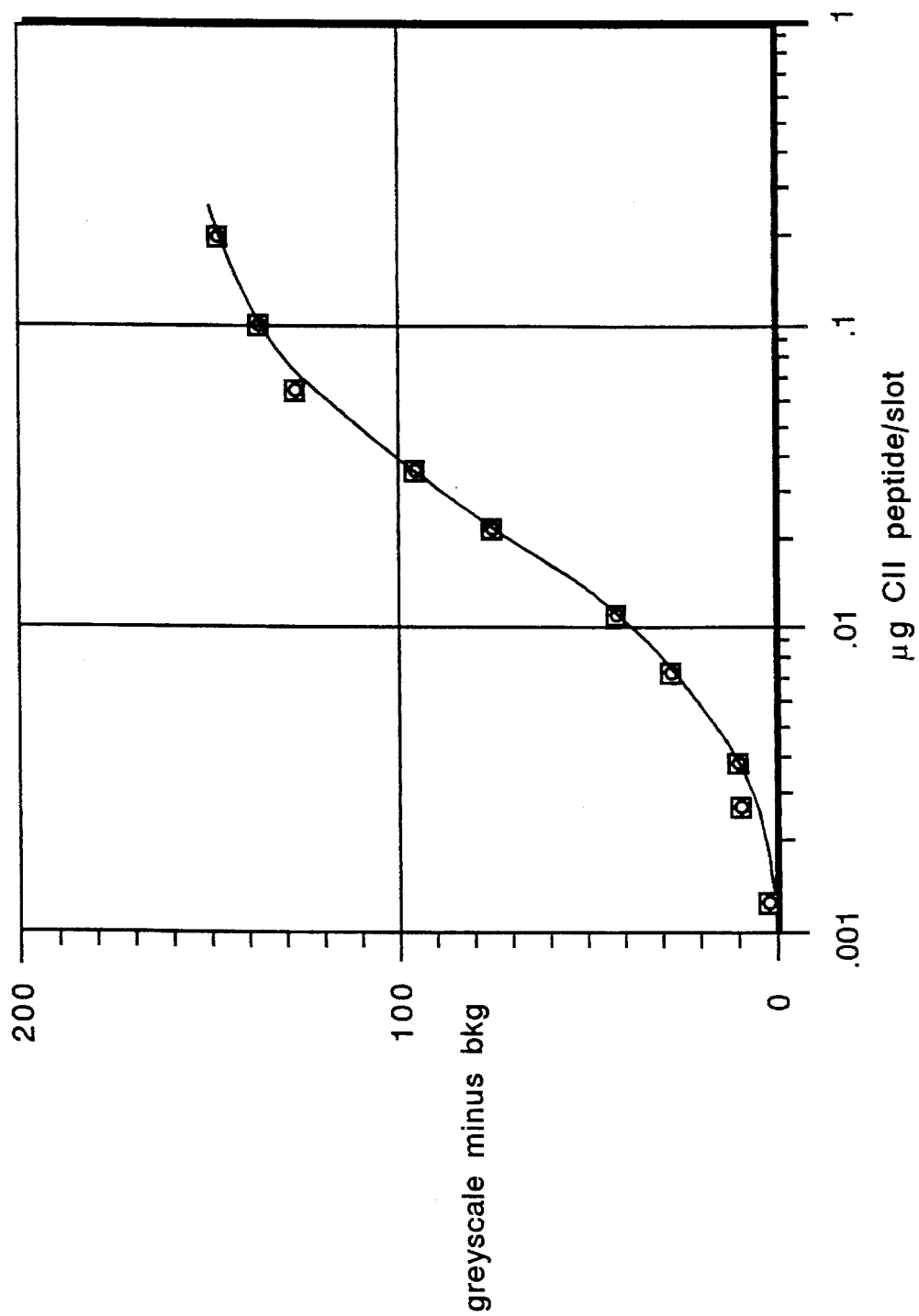
FIG. 17 is a graph showing a standard curve for total CNBr peptides by weight.

The membrane was analyzed by scanning into a MAC-LC computer and greyscale values were obtained using Image 1.44 software. Greyscale values of the samples were relate to the CII peptide standard curve. FIG. 17 shows a standard curve of CNBr peptides derived from Type II collagen. The standard curve was generated, using known concentrations of CNBr digested Type II collagen purified from calf articular cartilage and the monoclonal antibody E1E5. Each set of data on one membrane was analyzed using a standard curve generated on the same membrane to insure reproducibility.

Figure 18:
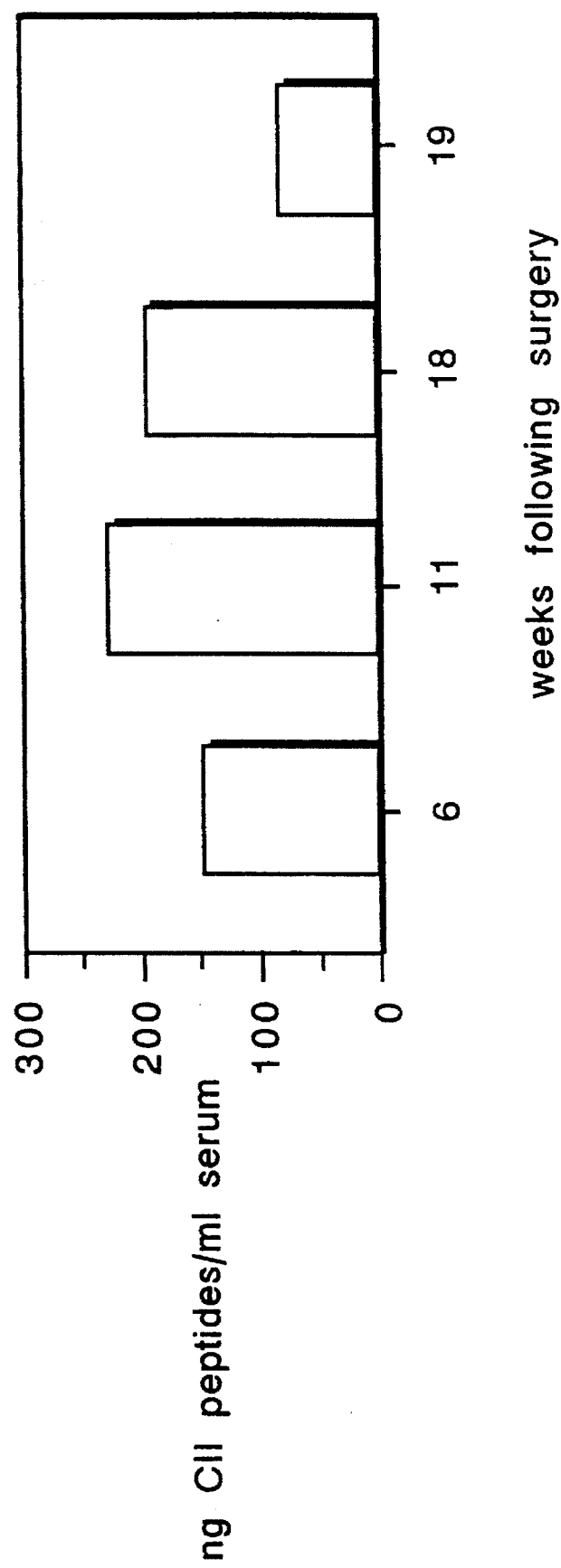
FIG. 18 is a graph showing Type II collagen peptides in the sera of rabbits with surgically induced osteoarthritis.

The assay showed that there was an increase of collagen Type II peptides after five and ten weeks in the sera of the rabbits with surgically induced osteoarthritis, followed by a decrease after eleven weeks (FIG. 18). These results indicate that we were able to measure collagen Type II peptides present in serum and the pattern of concentrations of the peptides is in agreement with the histological findings. The histology of the articular cartilage showed only the early stage of destruction at the end of the experiment.

EXAMPLE 7

The immunoassay described in Example 6 was used to study adjuvant-induced arthritis in rats.

Figure 19:
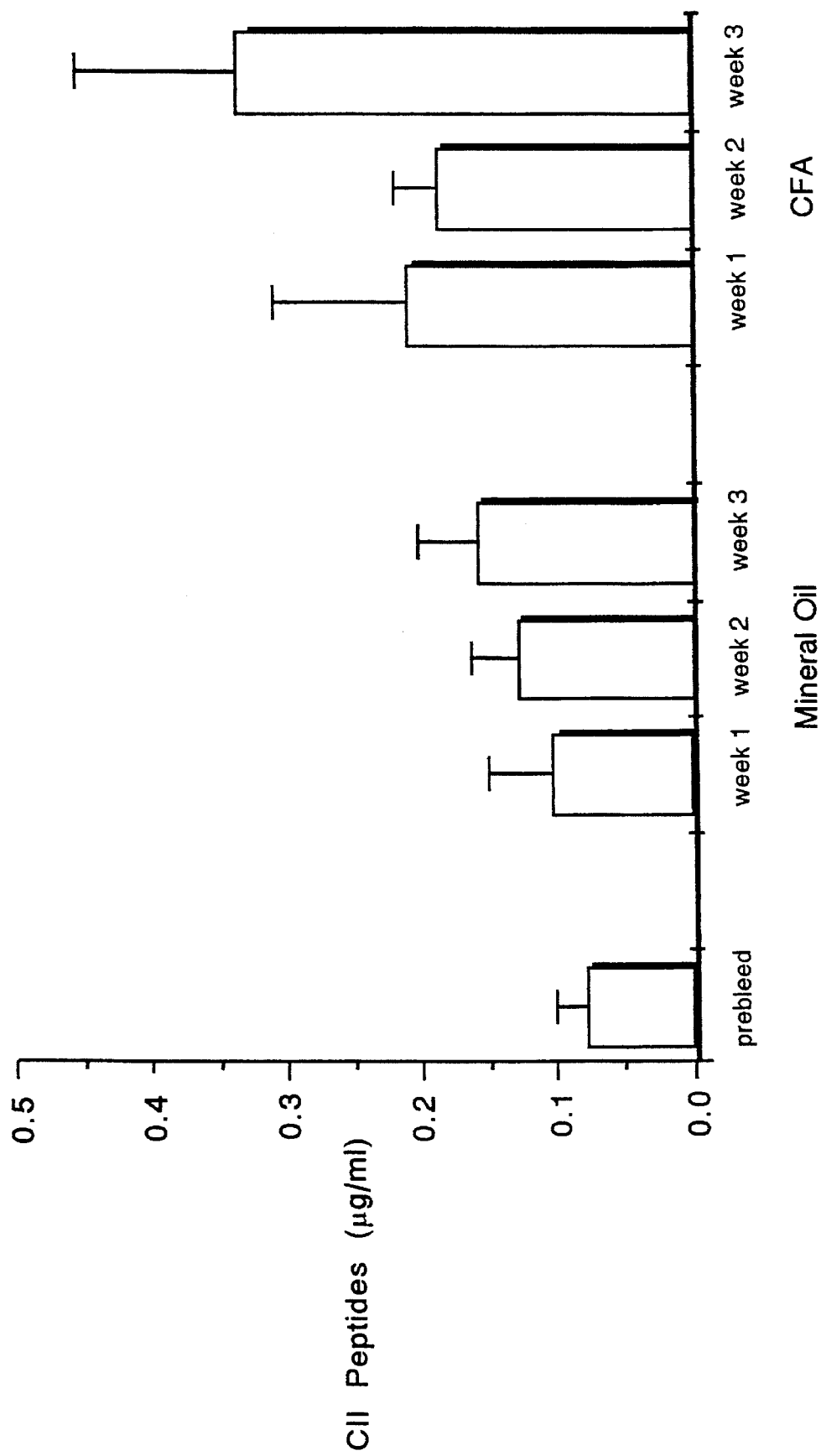
FIG. 19 is a graph showing Type II collagen peptides in the sera of rats with adjuvant-induced polyarthritis.

More specifically, rats were pre-bled and then injected with mineral oil (as controls) or with complete Freunds adjuvants in the foot pad of the right hind limb [see Pearson, C. M. Proc. Soc. Exp. Bio. Med. 91:95 (1956), hereby incorporated by reference] (prebleed n=12, treated animal n=6). After one, two and three weeks, serum from each animal was assayed for collagen Type II peptides. Even within the small animal numbers in each group there was a significant increase of peptides with time in the serum of the experimental animals (FIG. 19).

EXAMPLE 8

The immunoassay described in Example 6 was used to quantify collagen peptides in the serum of mice which had collagen-induced arthritis. The injection of collagen in combination with Interleukin is known to induce a very rapid cartilage breakdown in any hyaline cartilage containing tissue.

Figure 20:
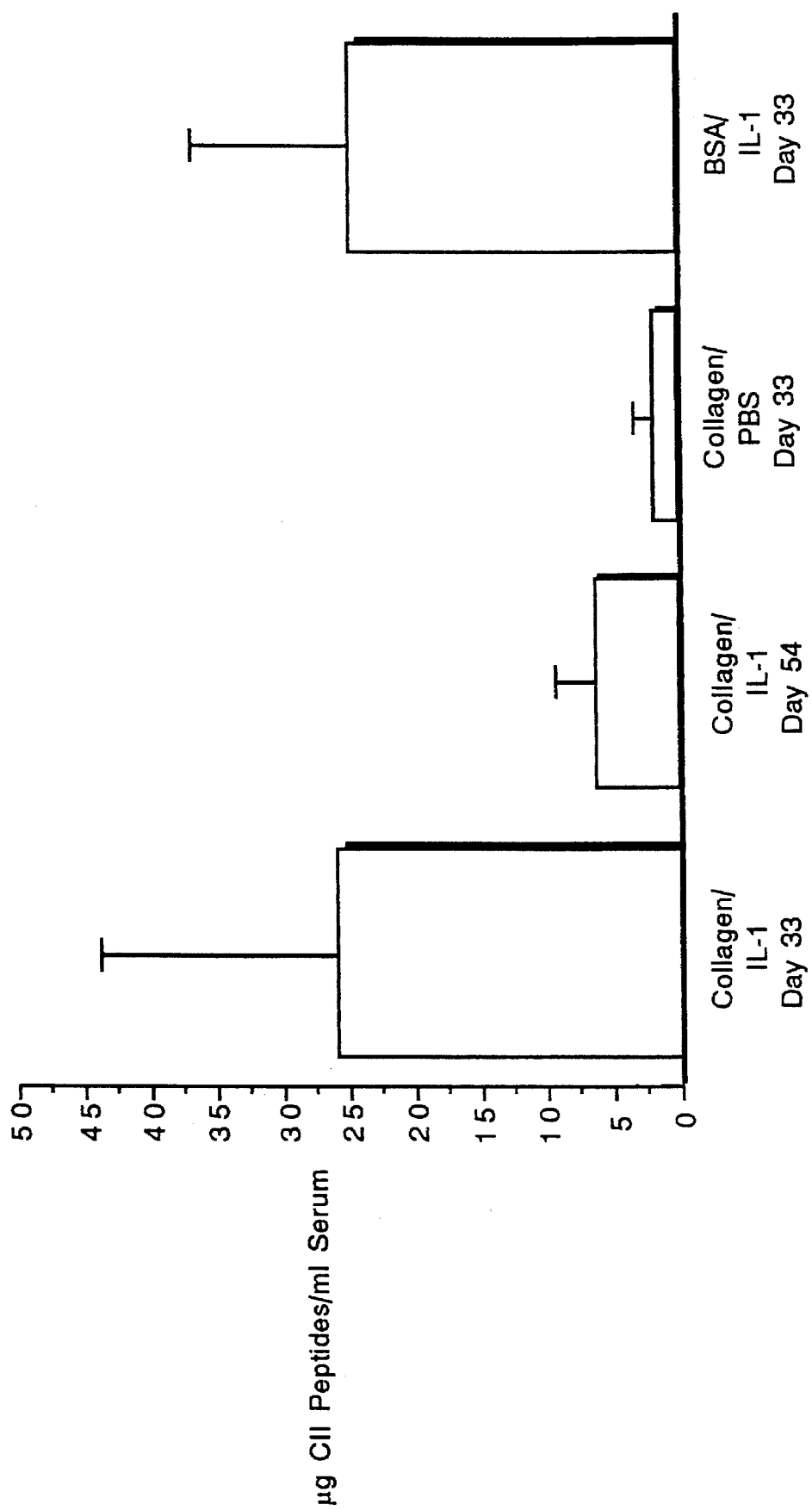
FIG. 20 is a graph showing Type II collagen peptides in the sera of mice with collagen-induced arthritis.

In the FIG. 20 experiment, mice were treated with collagen Type II (chicken) or bovine serum albumin (BSA) by subcutaneous injection at the base of the tail. The animals were injected the same after 3 weeks (boost). One week later recombinant Il-1 (1 ug) was injected subcutaneously for four days. Three days after the last injection, blood was drawn from the animals, i.e., day 33, and after additional 21 days, i.e., day 54 (n=6).

With our slot blot assay for collagen Type II peptides, we found a highly significant increase of peptides in the tested sera after 33 days of treatment with Interleukin when compared with the injection of collagen Type II alone (FIG. 20). At day 54, the concentration of collagen peptides decreased dramatically due to the depletion of cartilage. The articular cartilage as an example for all hyaline cartilage was evaluated by histological methods.

EXAMPLE 9

Collagen Type II peptides in the media from rat chondrosarcoma chondrocyte cultures detected by Western blot.

More specifically, media from rat chondrosarcoma chondrocyte cultures were concentrated by lyophilization, serum protein present from the addition of fetal calf serum was precipitated with TCA (final concentration 5%), desalted on a P2 column, and re-lyophilized. The Western blot showed one peptide band stained with the monoclonal antibody E1E5, which has a molecular weight higher than 15,000.

EXAMPLE 10

The serum samples from rats with adjuvant induced arthritis were treated with cold TCA (5%), followed by desalting and lyophilization of the supernatant as described in Example 9. After electrophoresis and Western blotting, the monoclonal antibody E1E5 stained a band above the CB8 band in the control lane, indicating a higher molecular weight than 15,000.

EXAMPLE 11

Carpal tunnel syndrome (CTS—entrapment neuropathy of the median nerve) represents a significant clinical problem. The presence of cartilage metaplasia within the carpal tunnel ligament in patients with CTS has been described histologically and has been seen in related disorders by cartilage specific immunohistochemical staining techniques. Sampson et al., J. Hand Surg. 16-A:714 (1991). This cartilage metaplasia is believed to represent a cellular adaptive transformation secondary to increased load mechanics on the tissues involved.

Specimens (1.0 cm×4 mm) of transverse carpal ligaments were obtained from patients undergoing a carpal tunnel release and patients undergoing surgery for adjacent, unrelated conditions. The lyophilized tissue was digested with 5x excess of CNBr (w/w) in 70% formic acid overnight at 40°. The samples were lyophilized twice and desalted over a P2 column. The CNBr peptides were then separated by PAGE on 16% polyacrylamide gels in a Bio Rad Minigel apparatus. Control digests of purified human collagen types I and III, as well as rat chondrosarcoma derived Type II collagen, were present on each gel. The protein bands were transferred to nitrocellulose membrane. The membrane was blocked with 5% nonfat milk followed by a first incubation with E1E5 monoclonal antibody and a second incubation with peroxidase labeled goat anti-mouse IgG. A chromophore mixture of 3,3'-diaminobenzidine and 4-chloro-1-naphthol was then added.

The staining of the Type CII peptides control bands with the antibody E1E5 showed CB8 as the most prominent band. E1E5 was also found to be specific for CB9,7 and stain other peptides crosslinked with CB9,7. The monoclonal antibody was nonreactive with CNBr peptides derived from human collagen types CI and CIII. The CNBr peptides derived from the sample ligaments only showed significant staining in the region of CB8 indicating the presence of Type II collagen peptides. Results on CNBr digest of pulleys from ten patients with carpal tunnel syndrome showed a range of intensity of the stain with E1E5 was used in Western blot. All stained bands were in the molecular weight range of CB8. These results indicate that different amounts of collagen Type II can be identified in the tissue samples.

EXAMPLE 12

Collagen Type II peptides can be first purified by immunoadsorption using Affi-Prep Hz Hydrazide Support (Bio-Rad) before its detection or quantification by slot blot. The following procedure is modified from the instruction booklet that accompanies the beads.

The antibody (E1E5) was dialyzed overnight against two changes of 0.02M sodium acetate, pH 5 containing 0.15M sodium chloride. Freshly prepared 0.5M sodium periodate was added to the dialyzed antibody (1:50 v/v) and oxidation was carried out in a foil covered container for one hour at room temperature with gentle shaking. Immediately after the oxidation, glycerol was added to the antibody (1:20 v/v) to stop the reaction. The oxidized antibody was dialyzed overnight against two changes of 0.1M sodium acetate, pH 4.5 containing 1M sodium chloride.

Just prior to coupling, 1 ml of a slurry of hydrazide-beads was transferred to a sintered glass funnel. The beads were washed twice with 10 volumes of distilled deionized water and twice with 10 volumes of 0.1M sodium acetate, pH 4.5 containing 1M sodium chloride. A slurry of the washed beads was transferred to a glass vial, the liquid removed from atop the beads and less than three volumes of oxidized E1E5 (containing less than 5 mg of antibody) was added to the beads. The beads were incubated with the antibody for 24 hours at 8° C. on Nutator shaker.

When coupling was complete, the supernatant was removed and the beads were washed three times with an equal volume of 0.02M sodium phosphate, pH 7 containing 0.5M sodium chloride. The efficiency of the coupling was determined and the beads were stored at 4° C. in 0.02M sodium phosphate, pH 7 containing 0.5M sodium chloride plus 0.02% sodium azide.

Glass Epoxy beads containing bound E1E5 thus prepared were blocked 30 minutes with 5% bovine serum albumen, washed three times with PBS and incubated with either PBS or serum in the presence or absence of added CII peptides. Following a 1 hour incubation with gentle agitation, the beads were washed three times with PBS, once with a 1:10 dilution of PBS and eluted directly (with 0.1M Glycine-HCl, pH 2.2) into Milliblot slots containing sodium phosphate buffer, pH 11 which was present to neutralize the eluate from the beads. After incubating the samples overnight at 8° C., the dry Milliblot slots were rinsed twice with Tris buffered saline containing Tween-20 (TBS-T). The membrane was removed from the apparatus, placed in a pan containing 50 ml TBS-T and gently agitated for 10 minutes. The washed membrane was blocked in 5% nonfat milk in TBS at room temperature for 45 minutes. After washing the membrane four times in TBS-T, it was incubated with the first antibody (E1E5) for 2 hours at room temperature, then washed three times in TBS-T, and incubated for 1½ hours with peroxidase labeled IgG. Finally, the membrane was washed three times with TBS-T, twice with TBS, and the substrate, hydrogen peroxide and 3,3'-diaminobenzidine with 4-chloro-1-naphthol (DAB-CN) in citrate-phosphate buffer, pH 6 was added. The membrane was analyzed by scanning into a MAC-LC computer and greyscale values were obtained using Image 1.44 software. Sodium phosphate buffer, pH 11 by itself was not observed to have any effect on the membrane. Further, the antibodies immobilized on the beads were shown to bind collagen peptides in the presence of serum.

EXAMPLE 13

An immunoadsorption-slot blot assay was performed in a manner similar to that described in Example 12 except that QuantAffinity Epoxide-Glass Beads (Rainin) was used instead of Affi-Prep Hz Hydrazide Support. The following is modified from Rainin Instrument Co. leaflet PI-83.

E1E5 was dialyzed against three changes of 0.8M sodium phosphate, pH 7 (to get rid of the sulfhydryls which were added to preserve the antibody) and the dialyzed antibody was added to a single layer of dry beads. Excess antibody was present and the beads were totally surrounded by the solution. Following an overnight incubation at room temperature on a Thermolyne shaker the liquid was removed, the beads were washed three times with 10 ml phosphate buffered saline, pH 7.6 and stored at 4° C. in the above buffer.

DEPOSIT

Under the terms of the Budapest Treaty on the International Recognition of the Deposit of Microorganisms for the Purpose of Patent Procedure, deposit of hybridomas E1E5 and C4F6 were made on Feb. 10, 1993 with the American Type Culture Collection (ATCC) of Rockville, Md., USA, where the deposits were given Accession Numbers HB11263 and HB11264, respectively.

Applicants' assignees represent that the ATCC is a depository affording permanence of the deposits and ready accessibility thereto by the public if a patent is granted. All restrictions on the availability to the public of the materials so deposited will be irrevocably removed upon the granting of a patent. The materials will be available during the pendency of the patent application to one determined by the Commissioner to be entitled thereto under 37 CFR 1.14 and 35 U.S.C. §122. The deposited materials will be maintained with all the care necessary to keep it viable and uncontaminated for a period of at least five years after the most recent request for the furnishing of a sample of the deposited materials, and in any case, for a period of at least thirty (30) years after the date of deposits or for the enforceable life of the patent, whichever period is longer. Applicants' assignees acknowledge its duty to replace the deposit should the depository be unable to furnish a sample when requested due to the condition of the deposits.

OTHER EMBODIMENTS

The above specific examples are, therefore, to be construed as merely illustrative, and not limitative of the remainder of the disclosure in any way whatsoever.

From the above description, one skilled in the art can easily ascertain the essential characteristics of the present invention, and without departing from the spirit and scope thereof, can make various changes and modifications of the invention to adapt it to various usages and conditions. Other embodiments are also within the claims.

We claim:

1. A monospecific monoclonal antibody or an Fab, F(ab')$_2$ or Fv fragment thereof, which (1) binds to a Type II collagen peptide, but does not bind to Type II collagen and (2) binds to a site within a sequence selected from the group consisting of Gly-Phe-Gln-Gly-Leu-Xaa-Gly-Xaa-Xaa-Gly-Xaa-Xaa-Gly SEQ ID NO:1 and Gly-Leu-Gln-Gly-Leu-Xaa-Gly-Xaa-Xaa-Gly-Xaa-Ser-Gly SEQ ID NO:2, wherein Xaa is Pro or Hyp.

2. The monoclonal antibody of claim 1, wherein said antibody binds to a site within the sequence Gly-Phe-Gln-Gly-Leu-Xaa-Gly-Xaa-Xaa-Gly-Xaa-Xaa-Gly SEQ ID NO:1.

3. The tnonoclonal antibody of claim 1, wherein said antibody binds to a site within the sequence Gly-Leu-Gln-Gly-Leu-Xaa-Gly-Xaa-Xaa-Gly-Xaa-Ser-Gly SEQ ID NO:2.

* * * * *

UNITED STATES PATENT AND TRADEMARK OFFICE
CERTIFICATE OF CORRECTION

PATENT NO. : 5,541,295

DATED : July 30, 1996

INVENTOR(S) : Hans-Jurgen Barrach and Clinton O. Chichester

It is certified that error appears in the above-identified patent and that said Letters Patent is hereby corrected as shown below:

ON THE TITLE PAGE:

ITEM [56] OTHER PUBLICATIONS:

left column, line 5 from the bottom, replace "569" with --369--;

left column, line 4 from the bottom, replace "TIMPL" with --Timpl, R.--;

right column, line 2, replace "Tpe" with --Type--;

right column, line 9, replace "$\beta$" with --$\alpha$--;

right column, line 19, replace "Kittelberg" with --Kittelberger--.

UNITED STATES PATENT AND TRADEMARK OFFICE
CERTIFICATE OF CORRECTION

Figure 4B:
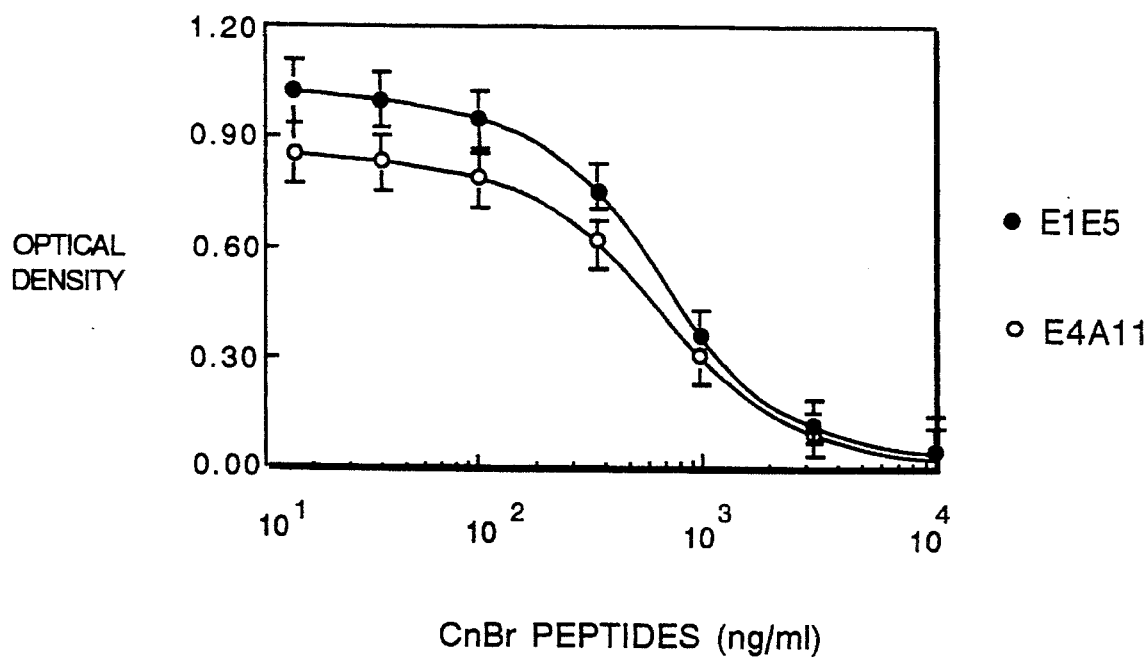

PATENT NO. : 5,541,295
DATED : July 30, 1996
INVENTOR(S) : Hans-Jurgen Barrach and Clinton O. Chichester It is certified that error appears in the above-indentified patent and that said Letters Patent is hereby corrected as shown below:

Fig. 4B, replace "CnBr" with --CNBr--.

Fig. 5A, replace "CnBr" with --CNBr--.

Fig. 5B, replace "CnBr" with --CNBr--.

Col. 2, line 58, replace "liters" with --liter--; and replace "10" with --$10^8$--.

UNITED STATES PATENT AND TRADEMARK OFFICE
CERTIFICATE OF CORRECTION

PATENT NO. : 5,541,295

DATED : July 30, 1996

INVENTOR(S) : Hans-Jurgen Barrach and Clinton O. Chichester

It is certified that error appears in the above-identified patent and that said Letters Patent is hereby corrected as shown below:

Col. 2, line 59, replace "liters" with --liter--.

Col. 2, line 62, delete "least"; and replace "liters" with --liter--.

Col. 3, line 38, replace "incorproated" with --incorporated--.

Col. 6, line 42, replace "CBe" with --CB8--.

Col. 7, line 17, replace "mg", both occurrences, with --$\mu$g--.

Col. 9, line 7, replace "mg" with --$\mu$g--.

Col. 9, line 21, replace "AgS" with --Ag8--.

Col. 9, line 43, replace "∞g" with --$\mu$g--.

Col. 10, line 17, replace "mg" with --$\mu$g--.

Col. 10, line 18, replace "∞g" with --$\mu$g--.

Col. 11, line 60, replace "(19923" with --(1992)--.

Col. 12, line 28, replace "-32,000" with --~32,000--.

UNITED STATES PATENT AND TRADEMARK OFFICE
CERTIFICATE OF CORRECTION

PATENT NO.  : 5,541,295

DATED       : July 30, 1996

INVENTOR(S) : Hans-Jurgen Barrach and Clinton O. Chichester

It is certified that error appears in the above-identified patent and that said Letters Patent is hereby corrected as shown below:

Col. 12, line 67, replace "Asp" with --Hyp--.

Col. 13, line 1, replace "Hyp" with --Xaa--, all four occurrences.

Col. 16, line 34, replace "B" with --$\beta$--.

Col. 18, line 27, replace "B" with --$\beta$--.

Col. 18, line 34, replace "mg" with --$\mu$g--.

Col. 26, line 48, replace "tnonoclonal" with --monoclonal--.

Signed and Sealed this

Twelfth Day of August, 1997

Attest:

Attesting Officer

BRUCE LEHMAN

Commissioner of Patents and Trademarks

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
    ( A ) LENGTH: 13
    ( B ) TYPE: amino acid
    ( C ) STRANDEDNESS:
    ( D ) TOPOLOGY: linear ( i x ) FEATURE:
    ( D ) OTHER INFORMATION: Xaa stands for either proline
        or hydroxyproline.

( x i ) SEQUENCE DESCRIPTION: SEQ ID NO: 1:

Gly Phe Gln Gly Leu Xaa Gly Xaa Xaa Gly Xaa Xaa Gly
     1               5                   1 0

( 2 ) INFORMATION FOR SEQ ID NO: 2:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa stands for either proline
            or hydroxyproline.

( x i ) SEQUENCE DESCRIPTION: SEQ ID NO: 2:

Gly Leu Gln Gly Leu Xaa Gly Xaa Xaa Gly Xaa Ser Gly
         1               5                   1 0

( 2 ) INFORMATION FOR SEQ ID NO: 3:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa stands for hydroxyproline.

( x i ) SEQUENCE DESCRIPTION: SEQ ID NO: 3:

Gly Phe Gln Gly Leu Xaa Gly Pro Xaa Gly Pro Xaa Gly
         1               5                   1 0